US008230867B2

(12) United States Patent
Mark

(10) Patent No.: US 8,230,867 B2
(45) Date of Patent: Jul. 31, 2012

(54) METHOD FOR PERFORMING A SURGICAL PROCEDURE

(75) Inventor: Joseph L. Mark, Indianapolis, IN (US)

(73) Assignee: Nico Corporation, Indianapolis, IN (US)

( * ) Notice: Subject to any disclaimer, the term of this patent is extended or adjusted under 35 U.S.C. 154(b) by 224 days.

(21) Appl. No.: 12/700,378

(22) Filed: Feb. 4, 2010

(65) Prior Publication Data

US 2011/0190814 A1    Aug. 4, 2011

(51) Int. Cl.
*A61B 19/00* (2006.01)
*A61B 17/14* (2006.01)
*A61B 17/08* (2006.01)

(52) U.S. Cl. .................... 128/898; 606/176; 606/214

(58) Field of Classification Search ............... 606/79, 606/167–180; 600/564–568; 604/268; 128/898
See application file for complete search history.

(56) References Cited

U.S. PATENT DOCUMENTS

| 3,990,453 | A | 11/1976 | Douvas et al. |
| 5,385,570 | A | 1/1995 | Chin et al. |
| 5,505,210 | A | 4/1996 | Clement |
| 5,702,420 | A | 12/1997 | Sterling et al. |
| 6,013,028 | A * | 1/2000 | Jho et al. .................. 600/204 |
| 6,132,448 | A | 10/2000 | Perez et al. |
| 6,875,173 | B2 | 4/2005 | Suddaby |
| 2009/0048622 | A1* | 2/2009 | Wilson ...................... 606/190 |
| 2011/0190801 | A1* | 8/2011 | Mark et al. ............... 606/170 |

OTHER PUBLICATIONS

LinkBio—Spine Instruments for SimpleCleanTM; at http://linkbio.com/LinkSpinalInstruments/simpleclean.htm dated Feb. 9, 2010.
Catalog for ClearFlushTM entitled Flushable Kerrison Rongeur; by Boss Instruments Ltd. Jan. 2007.
Webpage for Collagen Matric, Inc. entitled Science, Technology, Innovation dated Feb. 9, 2010 at www.collagematrix.com.
Wecome to Spinus, LLC—Inovators of Devices for Neurological and Orthopedic Surgery product ANDRE™; dated Feb. 9, 2010 at http://www.psinus.us/Product-Information/andre2.htm.
Pictures of Surgical Instruments—Kerrison Punch from www.surgical-instrument-pictures.com dated Feb. 9, 2010.
Publication for Aesculap Neurosurgery Pneumatic Kerrison, by Caroli, et al; publisher: Braun Sharing Expertise (2008).
Brochure from Dura Gen, Dural Graft Matrix; "The revoluntionary advance in cranial and spinal duraplasty," Integra NeuroScienses (6 pages).
Brochure for Duraplasty Solutions; DuraGen, by Integra (2 pages).
Non-Final Office Action dated Nov. 14, 2011 from U.S. Appl. No. 12/700,456.

* cited by examiner

*Primary Examiner* — Tuan Nguyen
(74) *Attorney, Agent, or Firm* — Rader, Fishman & Grauer, PLLC

(57) ABSTRACT

A method for conducting a surgical procedure is described herein. The surgical procedure includes creating a pathway through a nasal cavity, creating an opening through a section of skull that is connected to the nasal cavity, harvesting a portion of the skull formed by creating the opening to expose a dura layer of the brain, cutting a section of the dura layer to expose a section of brain tissue, and inserting a tissue resection device through the nasal cavity to take tissue samples from the exposed brain tissue. The dura layer is then secured over the exposed brain tissue so as to create a watertight seal and the previously harvested portion of the skull is inserted in in the opening and secured to the skull to close the opening.

19 Claims, 16 Drawing Sheets

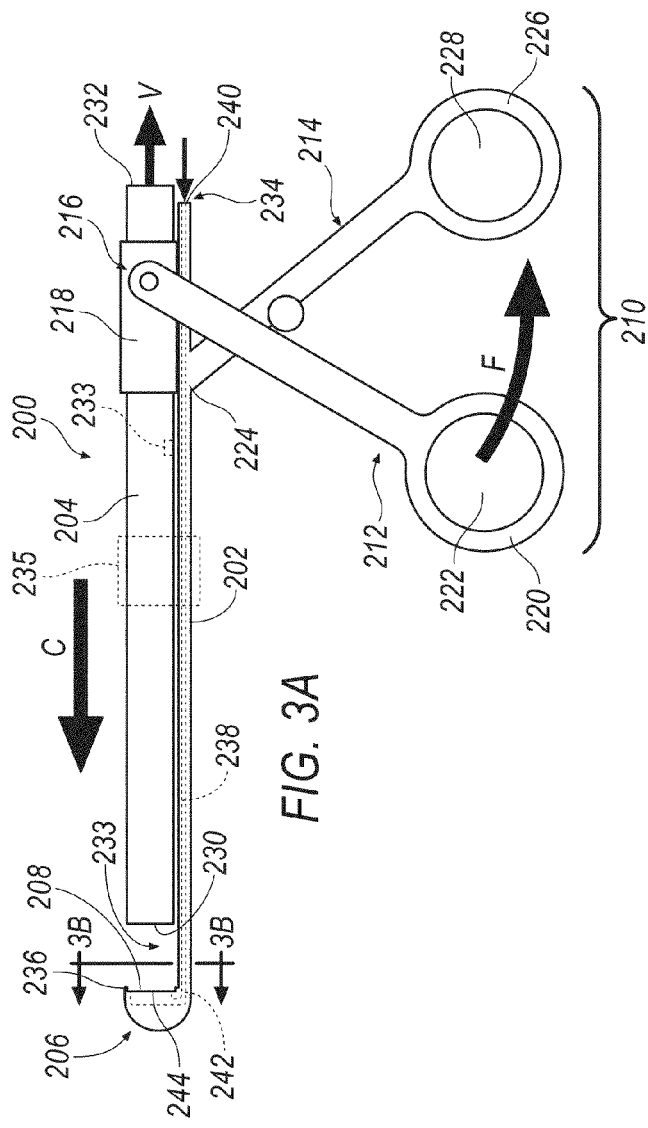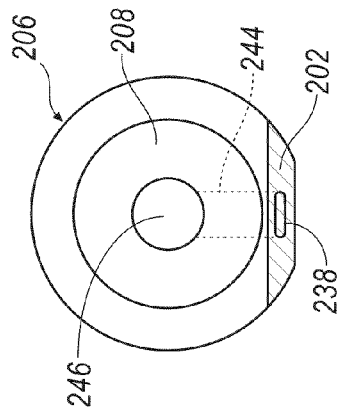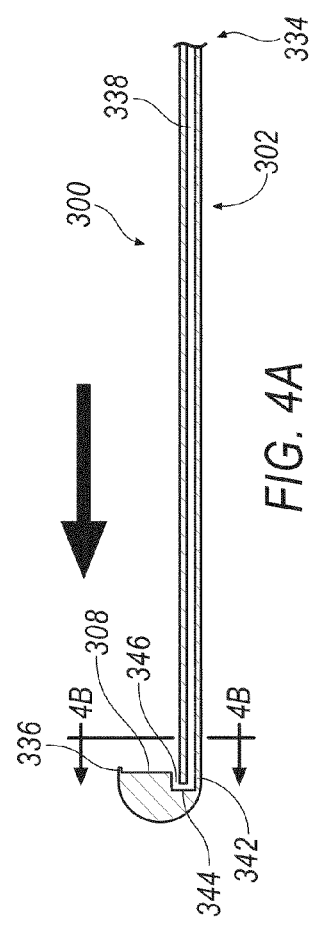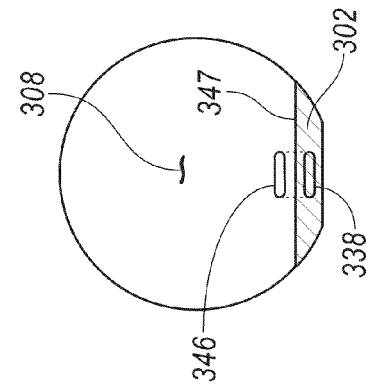

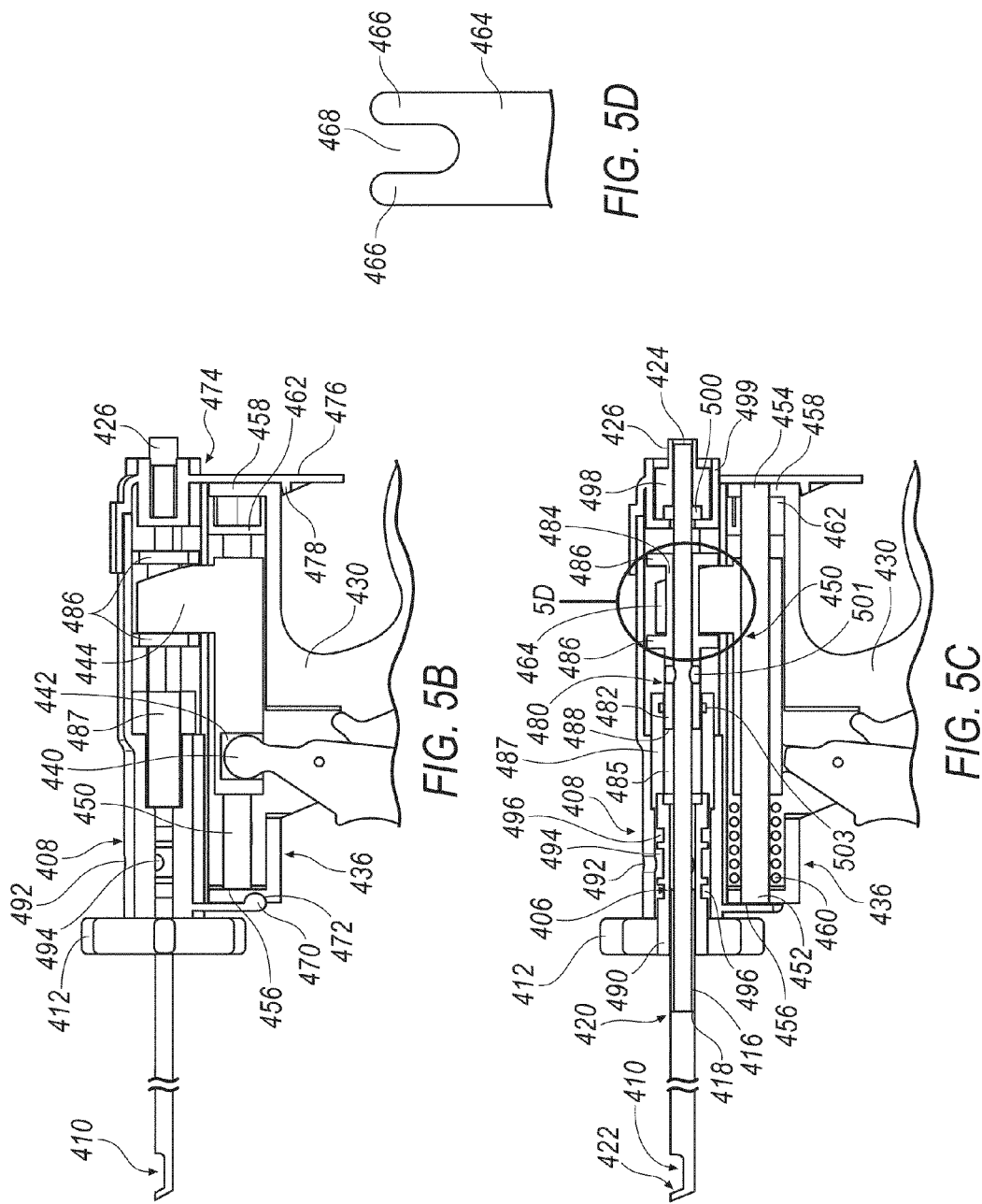

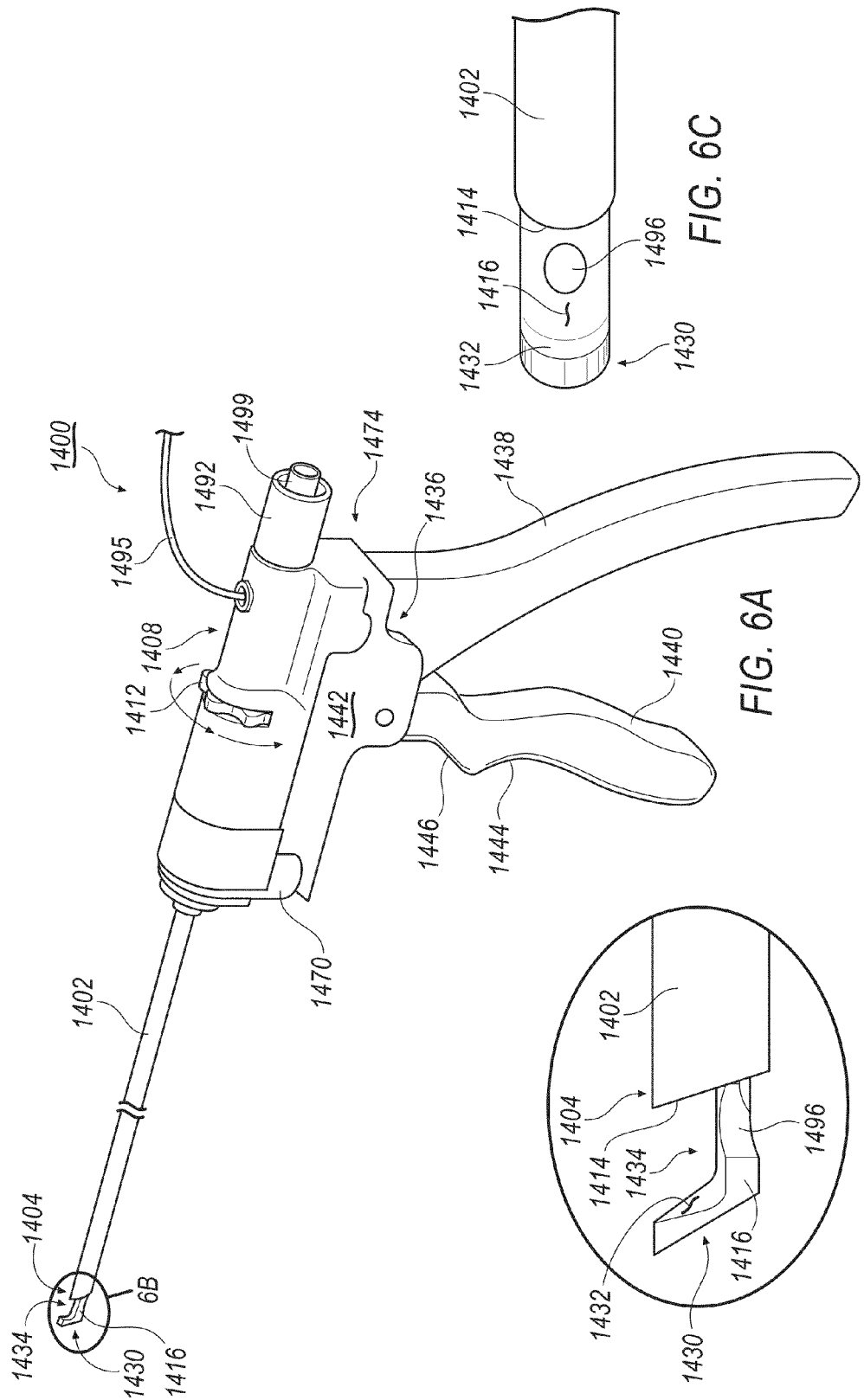

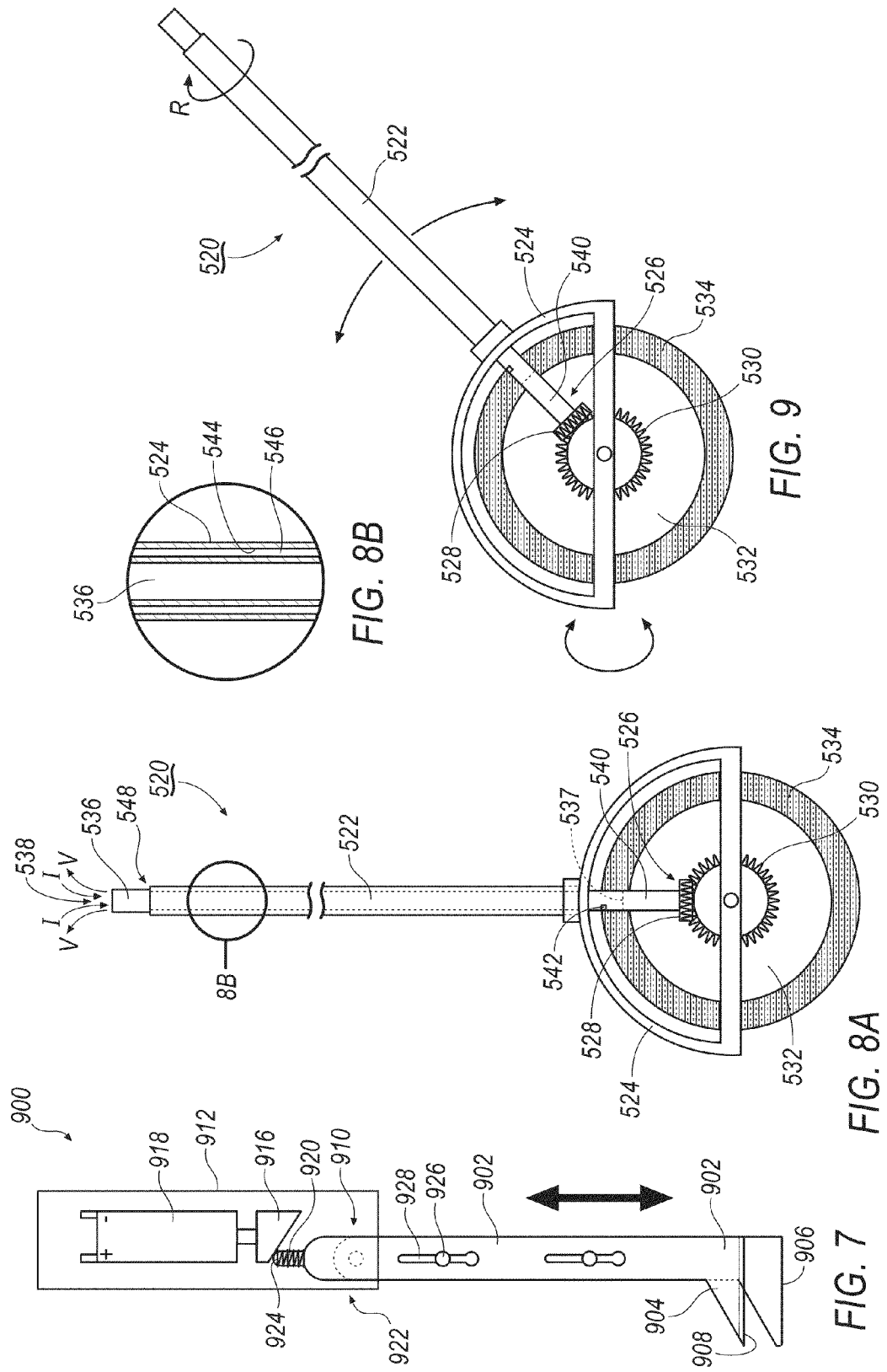

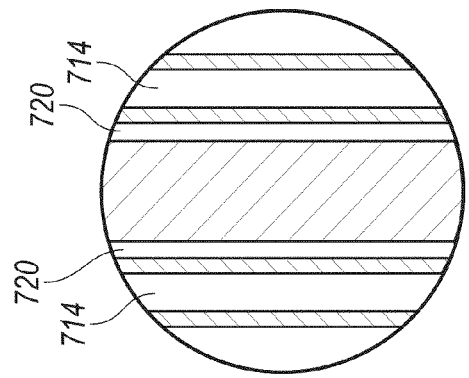
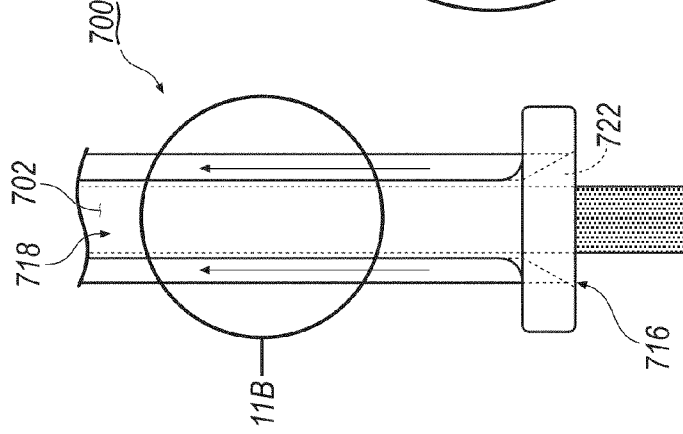
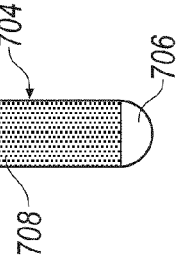
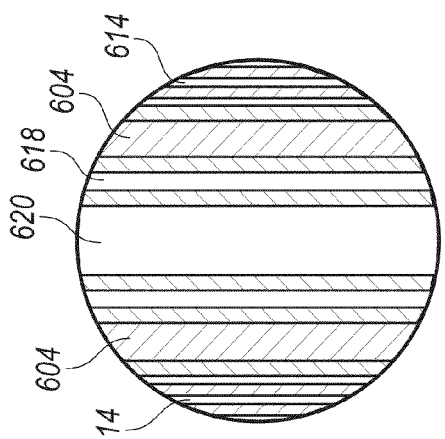
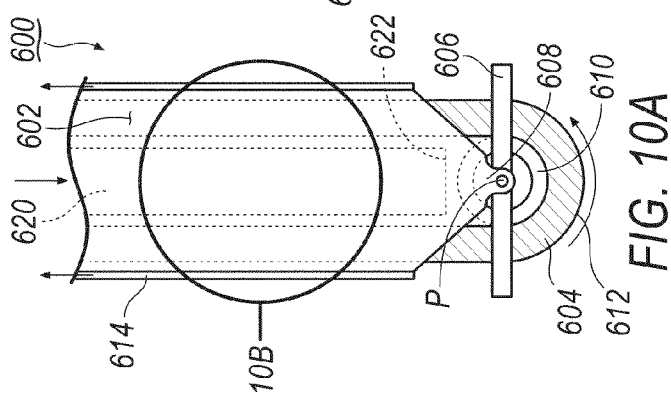
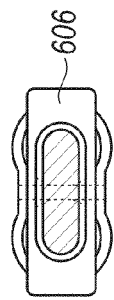

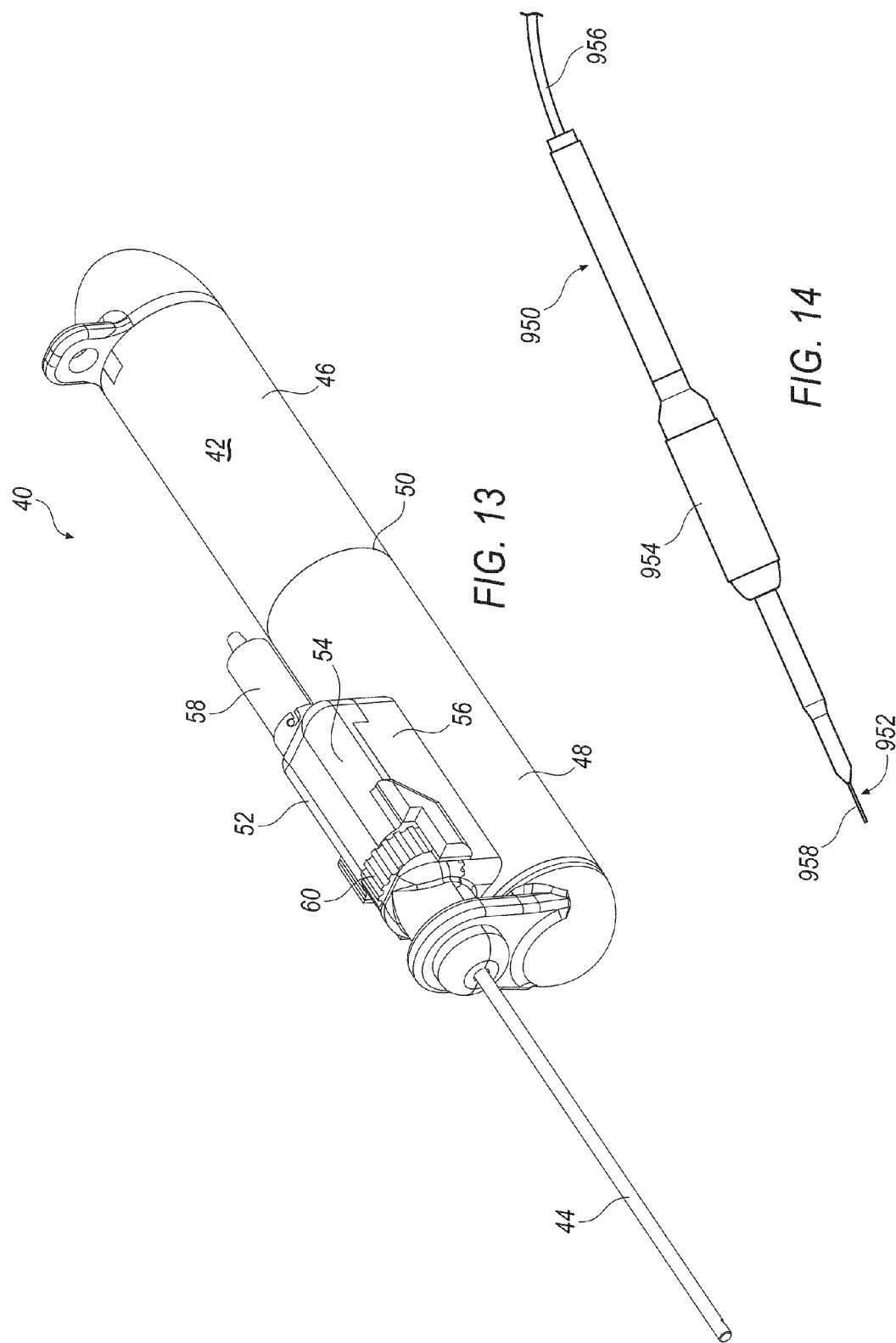

METHOD FOR PERFORMING A SURGICAL PROCEDURE

TECHNICAL FIELD

The present disclosure relates to a system and method for resection of tissue.

BACKGROUND

Various abnormalities of the neurological system, such as brain and spinal tumors, cysts, lesions, or neural hematomas, can cause severe health risks to patients afflicted by them, including deterioration in motor skills, nausea or vomiting, memory or communication problems, behavioral changes, headaches, or seizures. In certain cases, resection of abnormal tissue masses is required. However, given the complexity and importance of the neurological system, such neurosurgical procedures are extremely delicate and must be executed with great precision and care.

There a several different types of procedures that may be used to resect brain and spine tissue. One such procedure is open transcranial surgery; another is endonasal neurosurgery, whereby the neurosurgical procedure is conducted through the nose. Each procedure has its own advantages, depending on where an abnormality is located. For abnormalities associated with the pituitary gland, for example, an endonasal approach is particularly useful. A prior art endonasal neurosurgical procedure will now be explained, with reference to FIGS. 1 and 2.

Referring to FIGS. 1-2, first the anatomy of the nose 10 will be explained. As illustrated in FIG. 1, the nose 10 includes a plurality of turbinates 12 positioned within a nasal cavity 14. Access to nasal cavity 14 may be accomplished through the nostrils 16. Positioned beyond nasal cavity 14 is the cranium 18, a boney covering that protects the brain 20. Positioned in a central part of the brain is the pituitary gland 22. Situated between pituitary gland 22 and nasal cavity 14 is the sphenoid sinus 24, a cavity lined with mucus. A back wall of sphenoid sinus 24 is makes up an anterior wall of the sella turcica 26. Sella turcica 26 is a boney structure at the base of the skull in which pituitary gland 22 is positioned. Surrounding brain 20 and pituitary gland 22 is the dura 28. Dura 28 is a thin membrane that acts as a bag to contain cerebrospinal fluid.

In a prior art neurosurgery (and in spinal surgery), the following steps were performed. First, a pathway was formed. This is accomplished by using a punch device to remove tissues or boney material. In a prior art endonasal surgery, a punch device was used to remove one or more of the turbinates. Know punch devices, such as a Kerrison punch, include a slidable blade member that simply moves against a wall member so as to pinch a portion of the tissue (such as turbinates) therebetween. The slidable blade and wall member effectively grips and then tears the turbinate from its substrate in the nasal cavity. However, due to the size constraints of the nasal passages, the punch device must be small enough to be received within the nasal passage and only a limited amount of tissue may be removed with each sliding movement of the blade. Thus, after each punch operation, the punch device must be removed from the nasal passageway to remove the torn tissue from the punch device. Accordingly, multiple insertions must be made of the punch device (and multiple tissue removal operations) to clear the nasal passageway of the turbinates, lengthening the procedure and causing increased trauma to the patient, as well as increase bleeding in the nasal passageway. Further, to clear the bleeding and any mucoid secretions, insertion of separate section device was necessary, even further lengthening the procedure.

Once the pathway was created, the next step in a prior art endonasal surgery procedure is to create access to the brain. As shown in FIG. 2A, there are multiple access directions that can be taken to accomplish access to the brain. More specifically, the following approaches may be taken, the transcribriform $T_A$, the transpianum $T_B$, the transsphenoidal $T_C$, and the transclival $T_D$. The various approaches are the results of different directions through the sphenoidal sinus. 24. For surgical procedures whereby tissue adjacent the pituitary gland 22 (where a significant number of abnormalities are found) is to be resected, a pathway through the sella turcica 26 must be created.

In prior art systems, the sella turcica 26 is simply ground to dust, effectively eliminating a complete section of the boney structure to provide access to the dura layer of the brain. A slit is then formed in a section of the dura layer, to provide access to brain tissue.

Once the brain tissue is exposed, a resecting device is inserted through the nostril and nasal cavity and used to excise tissue. However, many known tissue cutting devices suffer from an inability to quickly and cleanly sever neurological tissue samples without causing "traction" or pull on the surrounding tissue. Like the Kerrison punch device, known tissue cutting devices often tear tissue, causing undesirable trauma to the surround tissue. In addition, many known devices are not configured to both "debulk" large structures and to finely shave smaller, more delicate structures and lack the flexibility needed in many procedures. Furthermore, many neurological procedures impose significant space limitations on the surgeon, and the tissue resection device needs to be manipulable by the surgeon with one hand in relatively small spaces. In some cases, known devices also emulsify resected tissue, rendering it unsuitable for subsequent analysis (e.g., histologic analysis).

Once tissue samples are excised and the procedure is completed, a fat graft is harvested from abdomen or a graft of muscle and fascia is harvested from the lateral thigh, causing additional trauma to the patient. The graft is placed in the hole that was formed in the sella turcica 26, effectively plugging the hole created by the removal of the boney structure. While the grafts serve to prevent subsequent leakage of cerebrospinal fluid, the brain is still more susceptible to trauma, as the grafts are less robust than the patient's original dura and boney structure making up the sella turcica 26, and the fat grafts must be packed sufficiently tight to create a watertight seal to prevent leakage of cerebrospinal fluid.

BRIEF DESCRIPTION OF THE DRAWINGS

Embodiments of the present disclosure will now be described by way of example in greater detail with reference to the attached figures, in which:

FIG. 3A is a side elevational view of an irrigating suction device.

FIG. 3B is a cross-sectional view of the irrigating suction device of FIG. 3A taken along lines 3B-3B.

FIG. 4A is a cross-sectional view of an alternative embodiment of an irrigating suction device.

FIG. 4B is a cross-sectional view of the irrigating suction device of FIG. 4A taken along lines 4B-4B.

FIG. 5B is a partial cross-sectional view of an actuating portion of the irrigating suction device of 5A.

FIG. 5C is another partial cross-sectional view of the actuating portion of the irrigating suction device of FIG. 5A.

FIG. 5D is an end view of area 5D from FIG. 5C.

FIG. 6A is a perspective view of an alternative embodiment of an irrigating suction device.

FIG. 6B is an enlarged side view of area 6B from FIG. 6A.

FIG. 6C is top view of a distal end of the irrigating suction device of FIG. 6A.

FIG. 7 is a side elevational view of a pair of surgical scissors.

FIG. 8A is an elevational view of a rotary saw.

FIG. 8B is an enlarged view of encircled area 8B taken from FIG. 8A.

FIG. 9 is an alternative view of the rotary saw of FIG. 8A.

FIG. 10A is partial view of an alternative embodiment of a rotary saw.

FIG. 10B is an enlarged view of the encircled area 9B taken from FIG. 10B in FIG. 10A.

FIG. 10C is end view of the rotary saw of FIG. 10A.

FIG. 11A is a partial elevational view of a burring device.

FIG. 11B is an enlarged view of the encircled area 10B taken from FIG. 11A.

FIG. 13 is a perspective view of a surgical device.

FIG. 14 is a perspective device of securing agent dispensing device.

DETAILED DESCRIPTION

Figure 1:
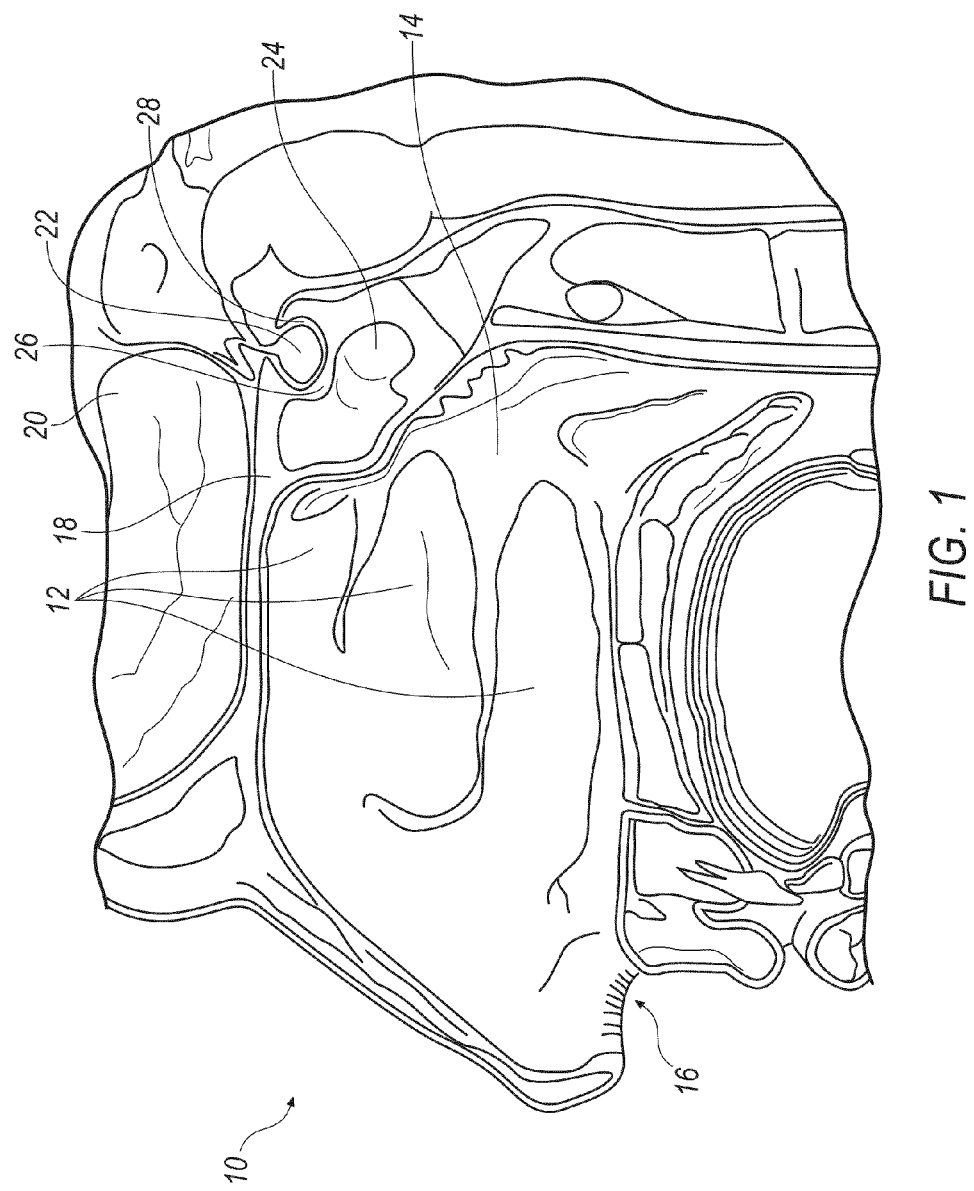
FIG. 1 is an exemplary cross-sectional view of a human nose.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein is a method of surgery, as well as various components of a system for use in same, including a tissue resecting device that is suited for neurosurgical applications such as the removal of spine and brain tissues. The components disclosed herein provide surgeons with an enhanced ability to minimize trauma to the patient, while providing effective and efficient minimally invasive surgical techniques. While described in the context of an endonasal neurosurgical procedure, it, is understood that various components and steps in the method may be practiced in other types of surgical procedures without departing from the disclosure. Thus, the description of an endonasal neurosurgical procedure is merely exemplary and the disclosure is not limited to such procedures.

Overview of Method of Performing Endonasal Surgery

Figures 2A, 2B:
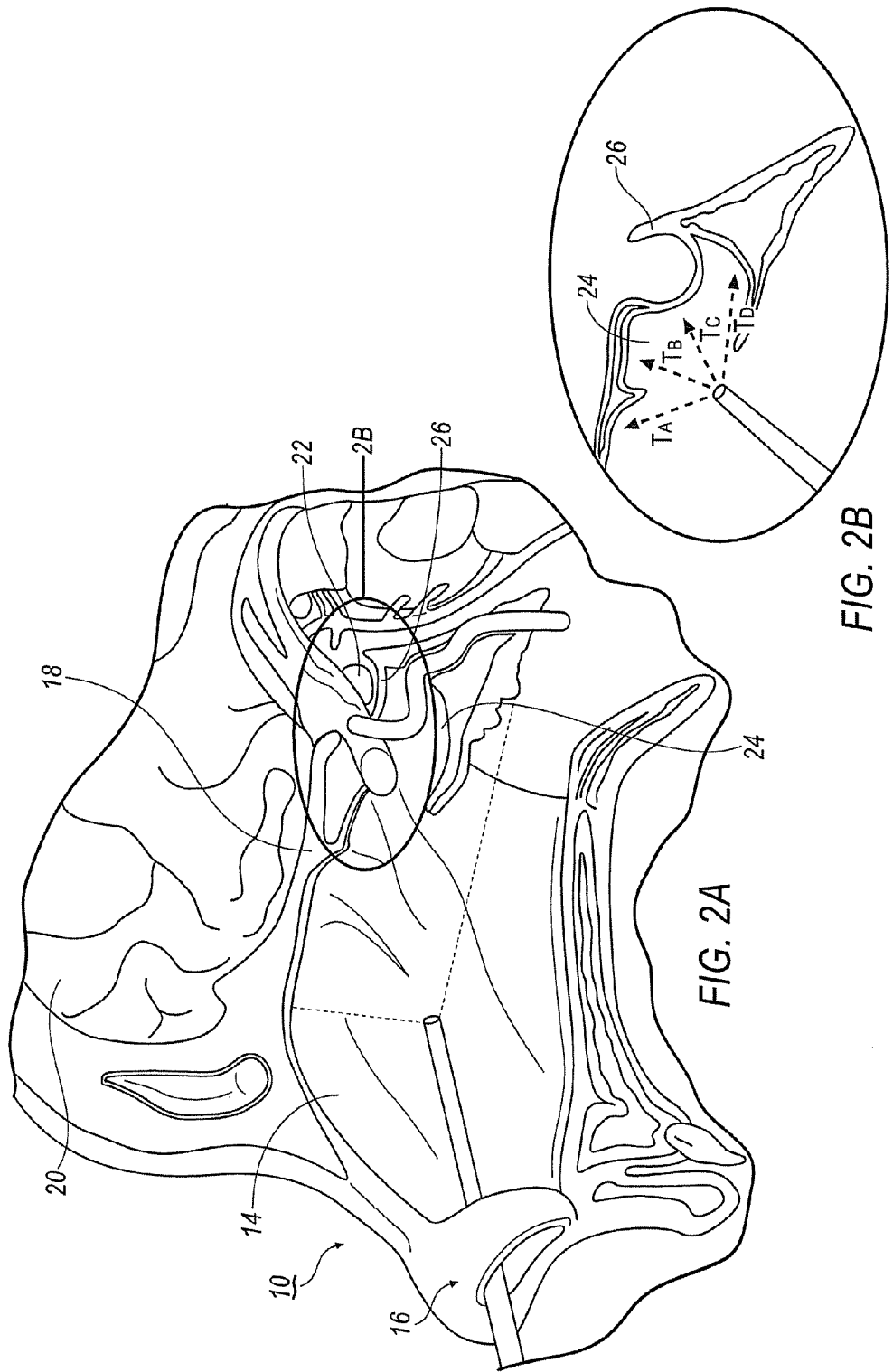
FIG. 2A is a cross-sectional view of a human nose after turbinates have been removed.
FIG. 2B is an enlarged view of the encircled area 2B from FIG. 2A, illustrating different approaches for conducting neurosurgery.

Referring to FIGS. 1-2 and the flowchart depicted in FIG. 15, an exemplary method 100 of performing endonasal surgery will be described. The method begins by first creating a pathway 102. In an endonasal surgery, the pathway is created through the nasal cavity 14. The pathway is created by removing soft and/or boney tissues, such as one or more of the turbinates 12, thereby creating access to the spenoidal sinus 24. Unlike prior art methods, the method 100 in the present disclosure uses a suction punch 200, 300, 400, 1400 to remove the turbinates 12 and other soft and boney tissues. The structure and operation of various embodiments of suction punches 200, 300, and 400, 1400 will be described in further detail below. As will also be explained, suction punches 200, 300, 400, 1400 may be configured to provide selective internal irrigation while tissue is being continuously cut from the substrate and removed from the patient. The irrigation serves to flush tissue through the suction punches 200, 300, 400, 1400 to prevent clogging of the devices and increase the speed of tissue removal. Thus, unlike prior art devices, multiple insertion and retraction of instruments into and out of the patient is minimized, thereby shortening procedures and minimizing trauma to the patient. Once the pathway is created, the process moves to step 104.

At step 104, an opening is created through the sella turcica 26 that forms the back wall of the sphenoid sinus cavity 24 to create access to the dura, and ultimately to brain tissue. This process is illustrated in FIG. 14A. In one exemplary embodiment, at step 104a, a starter hole 800 is first formed that is substantially smaller than an intended opening through the sella turcica 26, but large enough to insert a saw device therein. The starter hole 800 is created by grinding out a small portion of the boney structure of the sella turcica 26. The process then continues to step 104b.

Once the starter hole 800 is created, in step 104b, the saw device is inserted into the starter hole 800. The disclosed method may utilize several different types of saw devices. The structure and operation of various embodiments of saw devices 500, 600, 700, 800 developed by the applicants will be described in further detail below. The process then continues to step 104*c*.

In step 104*c*, once inserted into the starter hole, the saw device is operated to cut a section 804 of the sella turcica 26. However, unlike prior art methods where an opening was created solely by grinding the sella turcica 26 to dust, the saw device cuts such that the section of the sella turcica 26 is maintained as a unitary structure, defined by a peripheral edge 806, to create an opening 802. An example of an opening 802 created in step 104 is shown in phantom in FIG. 14A. The process then continues to step 105.

Once the section of the sella turcica 26 is cut, in step 105, the section 804 is harvested from sphenoid sinus cavity and removed from the surgical area, thereby exposing the dura layer 28, as shown in FIG. 14B. The process then proceeds to step 106.

Once the section of the sella turcica 26 is removed and the dura 28 is exposed, at step 106, a section 808 of the dura layer 28 is cut to provide access to the interior of the brain 20. Referring to FIG. 14C, unlike in prior art methods, whereby the dura is destroyed, in the instance method, the section 808 is cut so as to define a periphery of a flap 810 (shown in phanom). Surgical scissors 900 (an example of which is shown in FIG. 6 and which will be described in further detail below) may be employed to create the flap 810. The process then proceeds to step 107.

In step 107, as shown in FIG. 14D, the flap 810 is moved away from the dura layer 28 to expose a portion of the brain 20. An optional clip 812 (shown in phantom in FIG. 14D) may be used to anchor the flap 810 to an open position for ease of the procedure. The process then proceeds to step 108.

Figure 12:
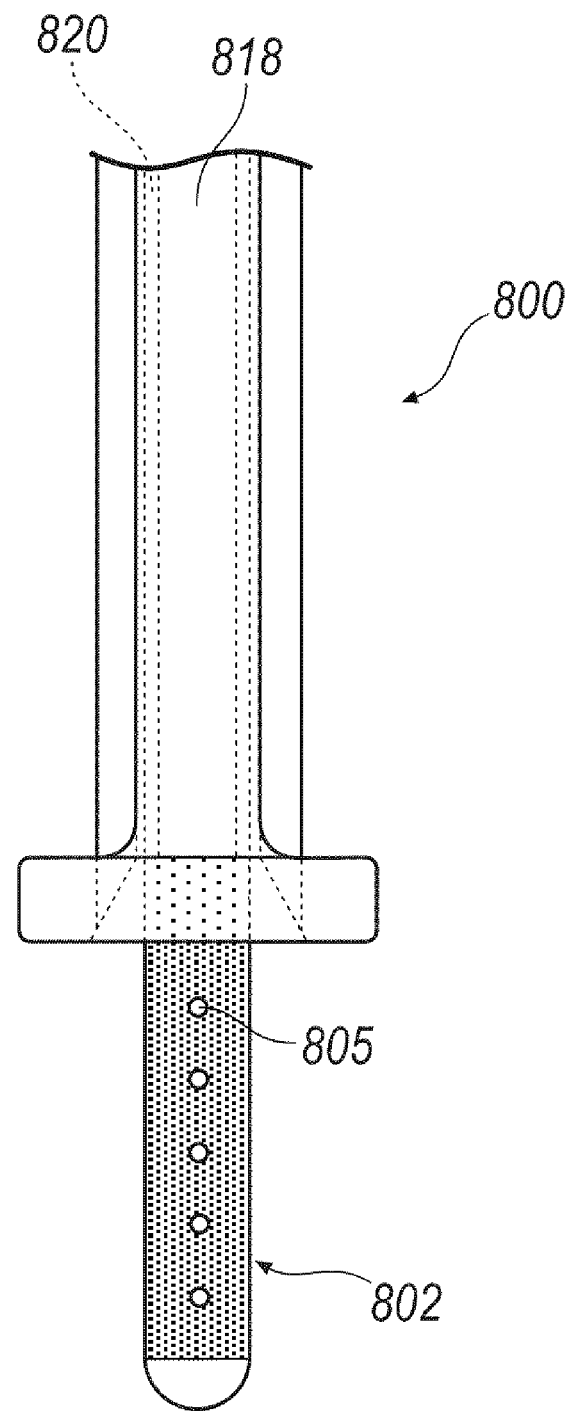
FIG. 12 is an alternative embodiment of a burring device.
Figure 15A:
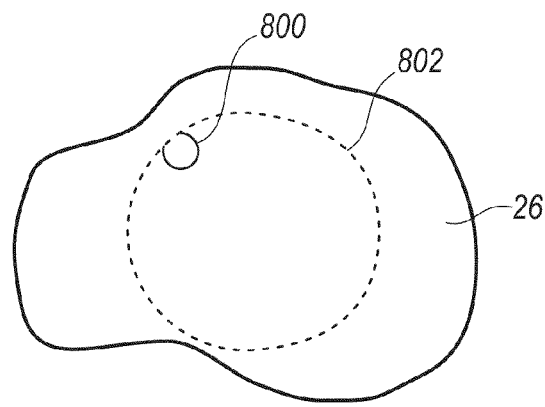
FIG. 15A is a perspective view of the creation of an opening in the sella turcica bone that protects the brain.
Figure 15B:
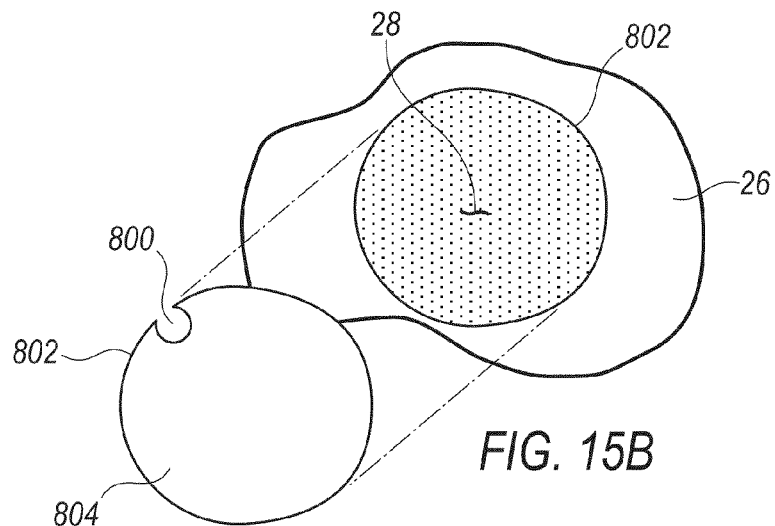
FIG. 15B is a partially exploded view of a section of the sella turcica being removed so as to create the opening in the sella turcica.
Figure 15C:
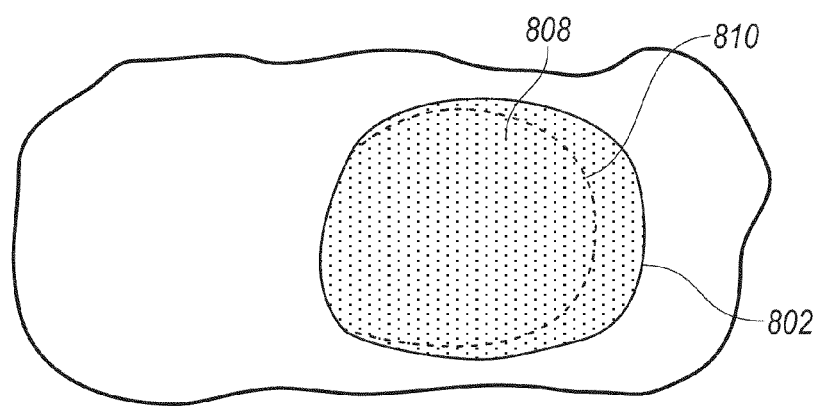
FIG. 15C is perspective view of the dura layer of the brain, as the dura layer is being cut to create a flap so as to expose a section of the brain.
Figure 15D:
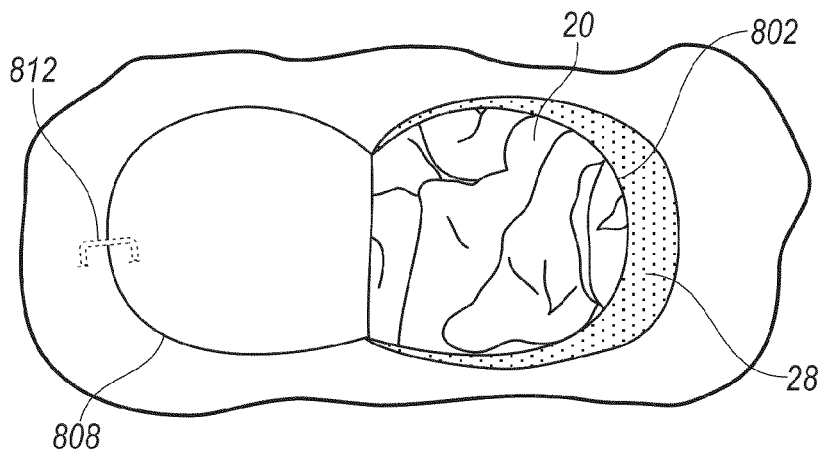
FIG. 15D is a perspective view of the flap of the dura layer pulled back to reveal a portion of the brain.
Figure 15E:
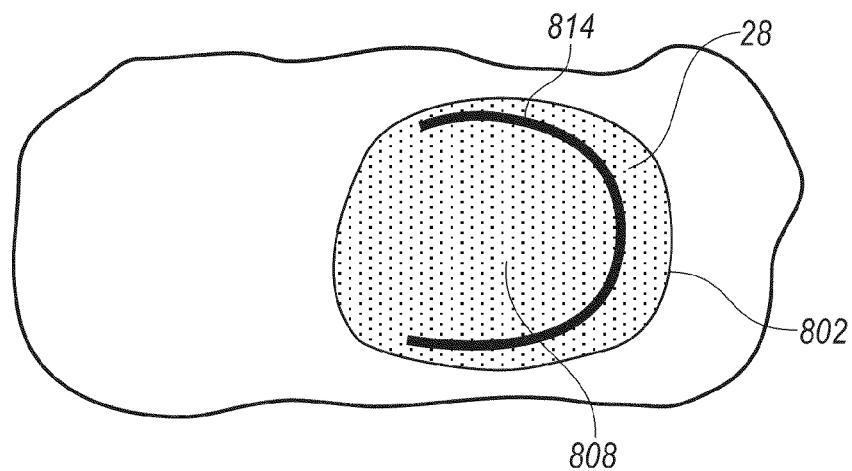
FIG. 15E is a perspective view of the flap of the dura layer secured to the remainder of the dura to create a watertight seal.
Figure 15F:
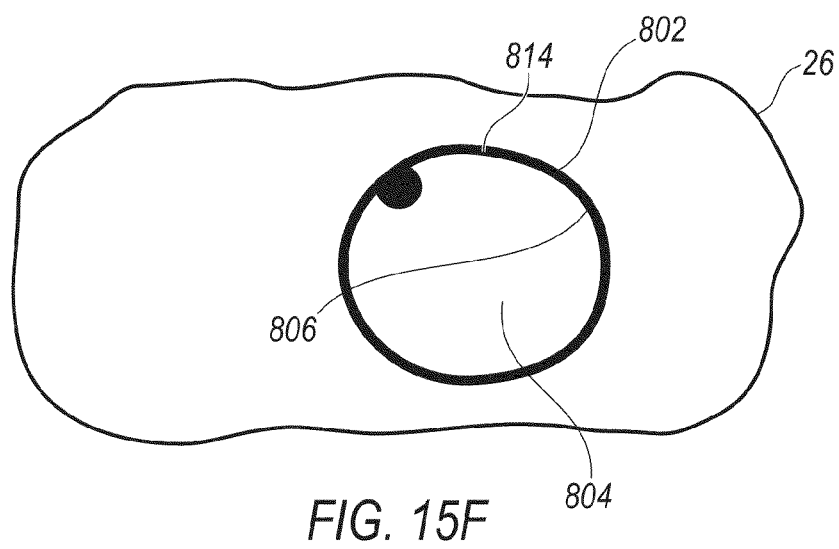
FIG. 15F is a perspective view of the bone section of the sella turscica that was previously removed from the surgical area, deposited within the opening created and secured therein.
Figure 16:
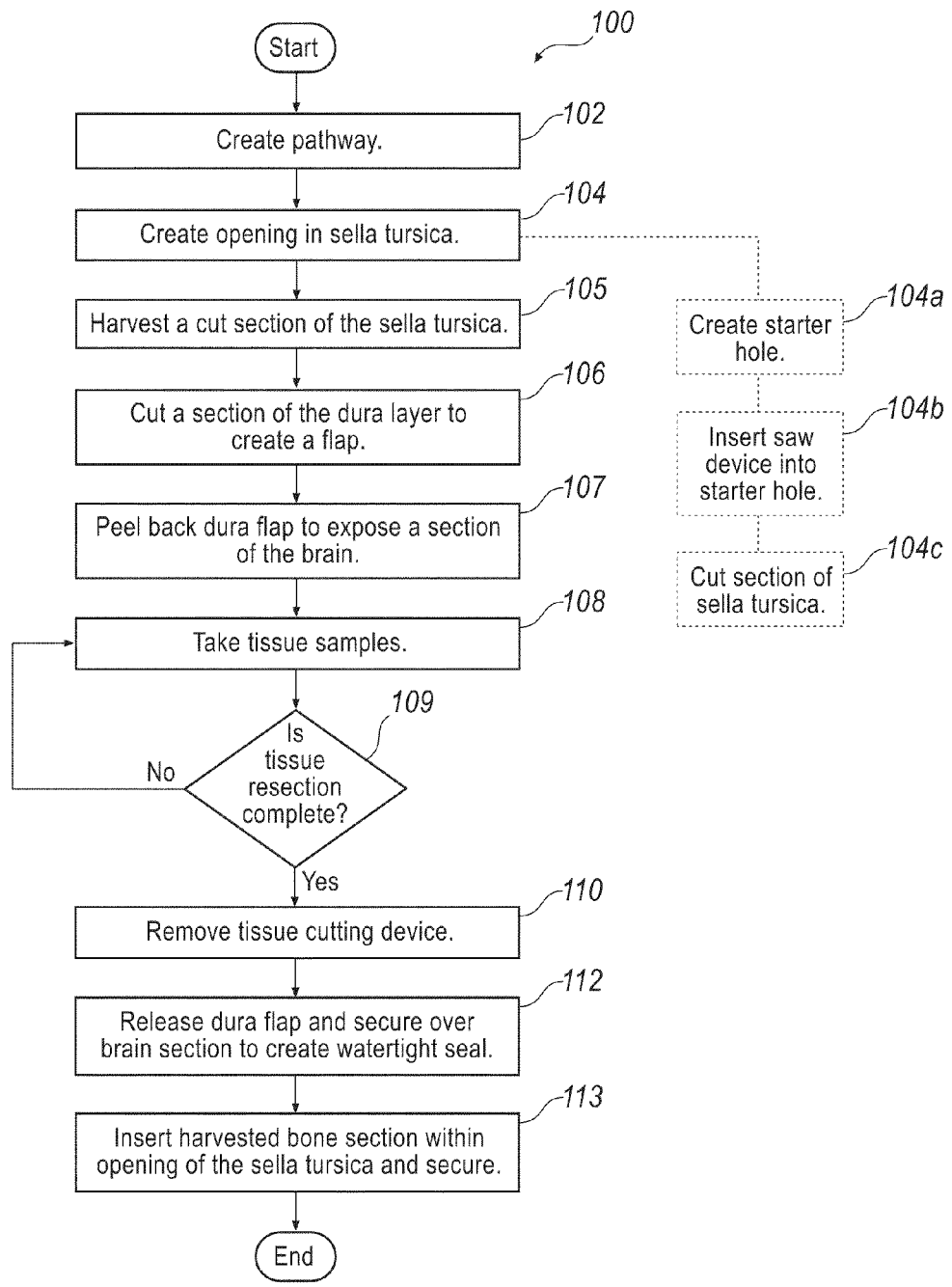
FIG. 16 is a flow chart illustrating a method of performing a surgical technique.

At step 108, with the brain portion 20 exposed, tissue resection may take place. More specifically, a tissue cutting device 40 may be employed to resect tissue from brain 20. Referring to FIG. 12, an exemplary tissue cutting device 40 is illustrated. Details of the tissue cutting device 40 are described below.

To resect tissue, a distal end of an outer cannula 44 is inserted through the pathway created through the nasal cavity 14, and through the sphenoid cavity 24 and sella turscica 26. The tissue cutting device 40 is operated such that an inner cutting cannula cooperates with outer cannula 44 to cut tissue and remove tissue samples from the brain in a minimally invasive manner. Once it is determined that tissue resection is complete (step 109), tissue cutting device 40 is then removed (step 110) from the patient and the process moves to step 112.

At step 112, the dura flap 808 is released or placed over the brain portion 20, as shown in FIG. 14E and secured. In one particular embodiment, a dispensing wand 900 (shown in FIG. 13) may be used to dispense a biocompatible glue and hemostatic agent 814 to secure flap 808 to the remainder of the dura layer 28. The glue promotes adhesion, while the hemostatic agent activates clotting to create a watertight barrier between the flap 808 and the dura layer 28 so as to maintain cerebrospinal fluid within the brain 20. This is unlike prior art methods whereby fat grafts are packed over the incision to create a watertight barrier, but left the patient vulnerable to leakage.

In yet another embodiment, a collagen matrix graft may also be used to secure the dura flap 808 to the remainder of the dura layer 28. More specifically, the collagen matrix graft may be overlayed over the flap 808 and secured by the glue and hemostatic agent mixture so as to create the watertight seal. As the dura heals, the collagen matrix allows ingrowth of tissue such that the collagen matrix is resorbed by the tissue. One suitable collagen matrix is sold by Integra under the tradename DuraGen. Once the flap 808 is secured, the process then advances to step 113.

At step 113, and unlike the prior art whereby the dura layer 28 remains exposed after conclusion of the procedure, in the present disclosure, the bone section 804 is replaced within opening 802 over the secured flap 808 and secured into the sella turcica 26. In one embodiment, dispensing wand 900 may be employed to dispense glue 814 to secure the bone section 804 in place. Alternatively, metal clips (not shown) may be used to secure the bone in place. The process then ends.

Overview of System Components for Endonasal Surgery

A. Suction Punch

As described above, one of the first steps in conducting a neurosurgical or spinal surgical procedure is to create a pathway to the tissue of interest. In an endonasal procedure, the example, one of the first steps involves removing one or more turbinates 12 positioned within the nasal cavity 14. To accomplish this task, referring to FIGS. 3A-3B, a suction punch is provided.

A first embodiment of a suction punch 200 includes a base member 202 and a selectively slidable cutting member 204 that slides on base member 202. A distal end 206 of suction punch 200 extends upwardly from base member 202 and forms a cutting surface 208.

Suction punch 200 further comprises an actuator assembly 210. Actuator assembly 210 comprises a first gripping member 212 and a second gripping member 214. First gripping member 212 includes a first end 216 that is pivotally connected to a sleeve 218. A second end 220 of the first gripping member 212 may be configured as a gripping member with an opening 222 for receiving a finger or thumb. Second gripping member 214 includes a first end 224 that is fixedly connected to base member 202. A second end 226 of the second gripping member 214 may also be configured as a gripping member with an opening 228.

Slidable cutting member 204 is defined by an open distal end 230 and an open proximal end 232. Slidable cutting member 204 is moveable between an open position and a cutting position. In the open position, distal end 230 is spaced away from cutting surface 208 to create a tissue receiving opening 233, as seen in FIG. 3A. In the cutting position, distal end 230 is slid into contact with cutting surface 208, thereby effectively closing tissue receiving opening 233 and cutting tissue that prolapses within tissue receiving opening 233 (to be explained below).

Distal end 230 is configured with a cutting edge sufficiently sharp to sever tissue, as will be explained in further detail below. Proximal end 232 is configured to receive a fitting (not shown) that is attached to a tubing line (not shown) that is operatively connected to a vacuum source. Accordingly, vacuum is delivered through cutting member 204 (indicated by arrow V) during operation of suction punch 200. Sleeve 218 is fixedly connected to cutting member 204 adjacent proximal end 232.

In operation, distal end 206 of suction punch 200 is inserted into the patient positioned adjacent tissue of interest. To insure proper placement of suction punch 200, suction punch 200 may be placed in the closed position prior to insertion (so as not to drag or snag tissue on cutting surface 208). While being inserted, the vacuum source is on, but may be vented to atmosphere to also prevent tissue from being pulled into suction punch 200 until properly positioned. To permit venting, an aperture 233 (show in phantom) may be formed through a sidewall of cutting member 204. When suction punch 200 is in the open position, the aperture is unblocked, to permit venting of the device. When suction punch 200 is in the closed position, aperture 233 is sealed off, thereby retaining vacuum. In one exemplary embodiment, a sealing sleeve 235 may be provided, whereby the sealing sleeve 235 (shown in phantom) is fixedly connected to base 202 and cutting member 204 is configured to slide therethrough. As cutting member 204 moves distally, aperture 233 slides into sealing sleeve 235, which may include a pair of seals, such as O'rings, at either end thereof. Once received therein, aperture 235 is effectively sealed and vacuum is restored to suction drive 200. Other configurations to provide selective venting is also contemplated. Once positioned, the vacuum is restored (by closing off the vent) and the suction punch 200 is placed in the open position. The vacuum source mechanically draws tissue into the tissue receiving opening 233. Next, the first gripping member 212 is actuated towards the second gripping member 214, as indicated by arrow F. This action causes cutting member 204 to slide along the base member 202 such that distal end 230 of cutting member 204 moves toward cutting surface 208 as indicated by arrow C. In one exemplary embodiment, cutting surface 208 is provided with a cutting lip 236 that cooperates with the cutting edge formed on distal end 230 of cutting member 204 to cleanly sever tissue.

Because suction device 200 is configured to deliver vacuum to tissue receiving opening 233, each manual cutting action automatically delivers the severed portions of the tissue (such as turbinates 12 for an endonasal approach) away from the patient. In one embodiment, a tissue filter (not shown) may be provided for retaining the severed portions of tissue. The tissue filter may be directly attached to the proximal end 232 of suction device 200. Alternatively, the tissue filter may be positioned remotely and operatively connected to the suction device 200 by tubing.

Unlike prior art punch devices, such as the Kerrison punch, only a single insertion of suction device 200 is required to sever any tissue in the desired pathway. Indeed, multiple tissue cutting actions can be accomplished with a single insertion. Thus, suction device 200 permits a speedier procedure, as well as less trauma to the patient.

To prevent tissue from occluding suction device 200, base member 202 may further be provided with an irrigation channel 238. Irrigation channel 238 extends from an open proximal end 240 of base member 240. Proximal end 240 may be configured to receive a fitting that is connected to an irrigation supply by tubing (not shown). A suitable irrigation supply may include saline or ringers.

Irrigation channel 238 further comprises a distal end 242 that adjoins an elongated mating channel 244 (best seen in phantom in FIG. 3B) formed adjacent cutting surface 208 in distal end 206 of suction device 200. Mating channel 244 is in communication with an opening 246 that extends through cutting surface 208.

In operation, irrigation is provided through irrigation channel 238 and delivered to tissue receiving opening 233. As the tissue is being severed, irrigation is being delivered to the tissue removed from the patient's body, lubricating the tissue and serving as a flushing mechanism to deliver tissue through suction punch 200 and prevent occlusion. Further, as discussed above, vacuum may also be applied to flush the irrigation fluid out of patient as suction device 200 operates.

Components of an alternative arrangement of a base member 302 of a suction punch 300 is shown in FIGS. 4A-4B. FIG. 4A is a cross-sectional view of base member 302. As may be seen, base member 302 is connected to a distal end 306 of suction punch 300, which defines a cutting surface 308. A cutting lip 336 may also be provided on cutting surface 308.

Like suction punch 200, base member 302 of suction punch 300 includes an irrigation channel that extends from a proximal end 334 along the length of base member 302 to a distal end 342. At proximal end 334, irrigation channel 302 is operatively connected to an irrigation supply, as described above in connection with suction punch 200. At distal end 342, irrigation channel connects to a groove 344 that adjoins an opening 346 foamed at a base 347 of cutting surface 308. Thus, in operation, irrigation fluid may be supplied to base 347 of cutting surface 308.

Figure 5A:
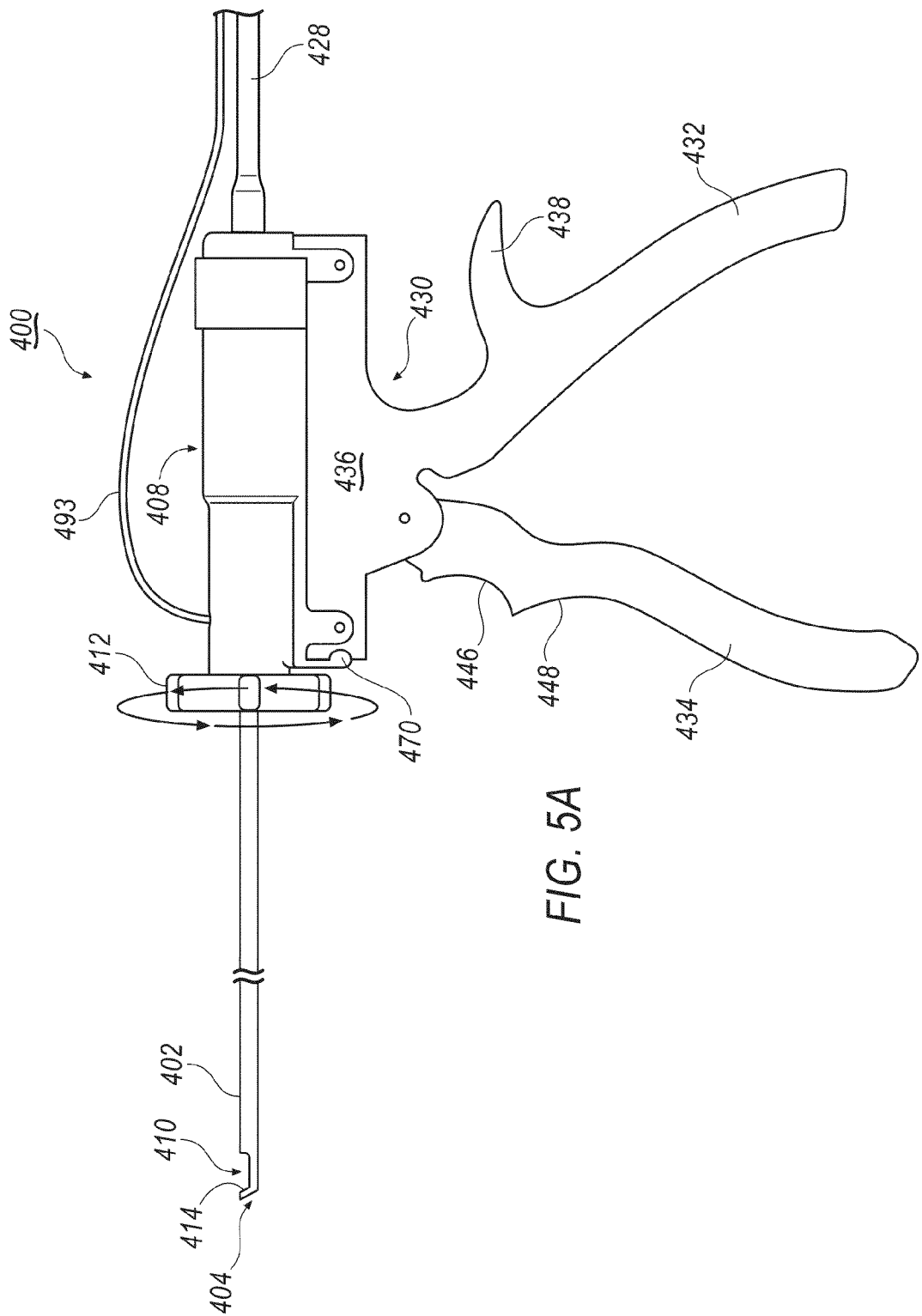
FIG. 5A is a side view of an alternative embodiment of an irrigating suction device.

Yet another alternative embodiment of a suction punch 400 is shown in FIGS. 5A-5C. Suction punch 400 includes an outer cannula 402 defined by a distal end 404 and a proximal end 406 (seen best in FIG. 5C), which is seated within a housing member 408 (to be explained in further detail below). A tissue receiving opening 410 is formed in outer cannula 402 adjacent distal end 404. Outer cannula 402 is configured for selective rotational movement. More specifically, a rotation dial 412 is fixedly secured to an outer surface of outer cannula 402. In one particular embodiment, a glue interference is used to fix rotation dial 412 to outer cannula 402. As rotation dial 412 is rotated, tissue receiving opening 410 is also rotated, thereby allowing for easy manipulation of suction punch 400 during procedures. Formed at distal end 404 of outer cannula 402, distally of tissue receiving opening 410, is a cutting surface 414.

Referring to FIG. 5C, disposed within outer cannula 402 is an inner cutting cannula 416. Inner cutting cannula 416 includes a cutting edge 418 disposed on a distal end 420 thereof. Cutting edge 418 cooperates with a distal edge 422 of tissue receiving opening 410 to sever tissue that is received within tissue receiving opening 410. A proximal end 424 of inner cutting cannula 416 is disposed in a fitting barb 426, to which a vacuum line 428 is operatively connected. Inner cutting cannula 416 is slidably seated within housing member 408. In other words, inner cutting cannula 416 is configured to selectively slide or reciprocate within outer cannula 402 during operation. However, inner cutting cannula 416 is also rotationally fixed with respect to outer cannula 402 such that rotation of rotation dial 412 also servers to rotate inner cutting cannula 416 with outer cannula 402.

Housing member 408 is mounted to an actuation member 430. Actuation member 430 comprises a first handle device 432 and a second handle device 434. First handle device 432 is fixedly connected to a shuttle housing 436. In one exemplary configuration, shuttle housing 436 is integrally formed with first handle device 432. First handle device 432 may further be configured with a thumb grip 438 for ease of use.

Second handle device 434 is pivotally connected to shuttle housing 436. Referring to FIG. 5B, a first end 440 is of second handle device 434 is received within a slot 442 that is formed within a selectively slidable shuttle member 444 that is disposed within shuttle housing 436. Second handle device 434 may be configured with gripping members 446 and 448 for ease of use.

Shuttle member 444 is mounted on a rod 450 (best seen in FIG. 5C) disposed in shuttle housing 436. Rod 450 is defined by a distal end 452 and a proximal end 454. Distal end 452 is fixedly secured to a distal face 456 of shuttle housing 436. Proximal end 454 is fixedly secured to a proximal face 458 of shuttle housing 436. A biasing member 460 is positioned on rod 450 distally of shuttle 444, so as to abut distal face 456 and a distal end of shuttle 444. Biasing member 460 (which may be a coil spring) serves to bias shuttle 444 into a retracted position, away from distal face 456. In one exemplary arrangement, a stop member 462 is secured to proximal end 454 of rod 450. Stop member 462 limits the distance that shuttle 444 may be retracted by biasing member 460. In one exemplary arrangement, actuation member 430 may be configured as a re-useable element.

Carried by, and fixedly secured to shuttle 444 is a carrier member 464. An end view of carrier member 464 is provided in FIG. 5D. Carrier member 464 includes upwardly extending wall members 466 that flank a mounting groove 468. Carrier member 464 extends upwardly from shuttle housing 436.

Housing member 408 is secured to shuttle housing 436. In one exemplary arrangement, housing member 408 includes a locking tab 470 that extends downwardly from housing member 408 and engages with a mounting groove 472 formed on a distal face 456 of shuttle housing 436. A proximal end 474 of housing member 408 may further include a downwardly extending wall member 476 that carries a snap protrusion 478 to grip a portion of the shuttle housing 436 (see FIG. 5B).

Disposed within, housing member 408 is mounting sleeve 480. Mounting sleeve 480 comprises an elongated section 482 that is connected to a mounting section 484. Disposed on either side of mounting section 484 are flange members 486. Mounting section 484 is received within mounting groove 468 carrier member 464. A distal end 488 of elongated section 482 is slidably received within a channel 485 formed in a mating sleeve 487. Mounting sleeve 480 is fixed secured to an outside surface of inner cutting cannula 416. To insure that inner cutting cannula 416 rotates with outer cannula 402, elongated section 482 is provided with a keyed surface that mates with a corresponding keyed surface formed in channel 484 (not shown). Thus, inner cutting cannula 416 may still selectively slide within channel 484 (and ultimately outer cannula 402), but not rotate independently of mating sleeve 487.

An internal hub member 490 is provided within housing member 408. Hub member 490 has a first end fixed to rotary dial 412 and a second end fixed to mating sleeve 487. Proximal end 406 of outer cannula 402 is secured in hub member 490.

Formed through housing member 408 is an irrigation port 492 that is in communication with an opening 494 in the hub member 490. In operation, irrigation (such as warm water, saline or ringers) enters into housing member 408 and into hub member 490 to deliver irrigation within the space between the inner cutting cannula 416 and the outer cannula 402. Sealing members (not shown), such as O-rings, may be disposed in grooves 496 disposed on either side of opening 494 to insure that the irrigation is directed between outer cannula 402 and inner cutting cannula 416.

Disposed at the proximal end of suction punch 400 is a fitting member 498 that is disposed in a fitting housing 499. The fitting member 498 carries fitting barb 424 and is configured with mounting grooves 500 that receive seal members (not shown). As discussed above, a vacuum line 428 is connected to the fitting barb 424 to deliver vacuum to inner cutting cannula 416. The seal members that are disposed in grooves 500 serve to insure that the vacuum is delivered to the inner cutting cannula 416.

Inner cannula 416 may also be provided with a vent aperture 501 to provide selective venting of suction device 400. When inner cannula 416 is retracted from tissue receiving opening 410 (as shown in FIG. 5C), vent aperture 501 is opened. However, when inner cannula 416 is in a cutting position (i.e., when distal end 418 is contacting cutting surface 422), vent aperture 501 becomes sealed off. More specifically, in one exemplary mounting sleeve 480 is moved out of channel 485 of mating sleeve 487, at least enough to expose venting aperture 501 that extends through both mounting sleeve 480 and inner cannula 416. When inner cannula 416 is advanced during the cutting stroke, venting aperture 501 is received with mating sleeve 487, distally of a sealing member (not shown) disposed in mounting grooves 503. In this configuration full vacuum is delivered through inner cannula 416.

During operation of suction device 400, second handle device 434 is retracted towards first handle device 432. This action causes shuttle 444 to move forward, against biasing member 460. As shuttle 444 moves forward, carrier member 464 pushes against one of the flanges 486 of mounting sleeve 480. As mounting sleeve 480 is fixedly secured to an outer surface of inner cutting cannula 416, inner cutting cannula 416 is advanced distally within outer cannula 402 toward tissue receiving opening 410, until distal end 420 of inner cutting cannula 416 contacts cutting surface 414 of outer cannula 402, thereby severing tissue that is disposed with tissue receiving opening 410. Repeated retraction and releasing of second handle device 434 results in repeated cutting action.

As discussed above, to facilitate severing of tissue, vacuum is delivered to inner cutting cannula 416 through vacuum line 428. The vacuum serves to draw tissue into tissue receiving opening 410, as well as removing cut tissue from tissue receiving opening 410 to a collection chamber (not shown) attached to vacuum line 428. Continuous vacuum permits multiple severing actions to be employed with a single insertion. However, delivery of continuous vacuum may be controlled by the action of the cutting cannula. More specifically, the action of the inner cutting cannula provides for a venting action that relieves vacuum. As such, the device is particularly useful in navigating near and around critical structures within the patient so as not to inadvertently remove such structures during procedures. In addition, by providing the capability of multiple severing actions, procedure time may be reduced.

To alleviate removed tissue occluding the aspiration pathway during the cutting action, irrigation may be provided via an irrigation port 492 that is connected to an irrigation supply by an irrigation line 493, between the inner cutting cannula 416 and the outer cannula 402. The irrigation fluid, which may be warm water, saline or ringers, serves to flush the tissue during the procedure. To provide flexibility in accessing the tissue or boney structure, rotation dial 412 permits the user to selectively rotate tissue receiving opening 410 to a desired location within the nasal cavity 14.

Yet another alternative embodiment of a suction punch 400 is shown in FIGS. 6A-6H. Suction punch 1400 includes an outer cannula 1402 defined by a distal end 1404 and a proximal end 1406 (best seen in FIG. 6F), which is seated within a housing member 1408 (to be explained in further detail below). Distal end 1404 is open and may have an angled cutting edge 1414 to provide increased cutting effectiveness, to be explained below in further detail.

Outer cannula 1402 is configured for selective rotational movement. More specifically, a rotation dial 1412 is operatively secured to outer cannula 1402 (to be explained below in further detail). As rotation dial 1412 is rotated, distal end 1404 is also rotated, thereby allowing for easy manipulation of suction punch 1400 during procedures. Outer cannula 1402 is also configured for reciprocal movement, also to be explained below in further detail.

Figure 6D:
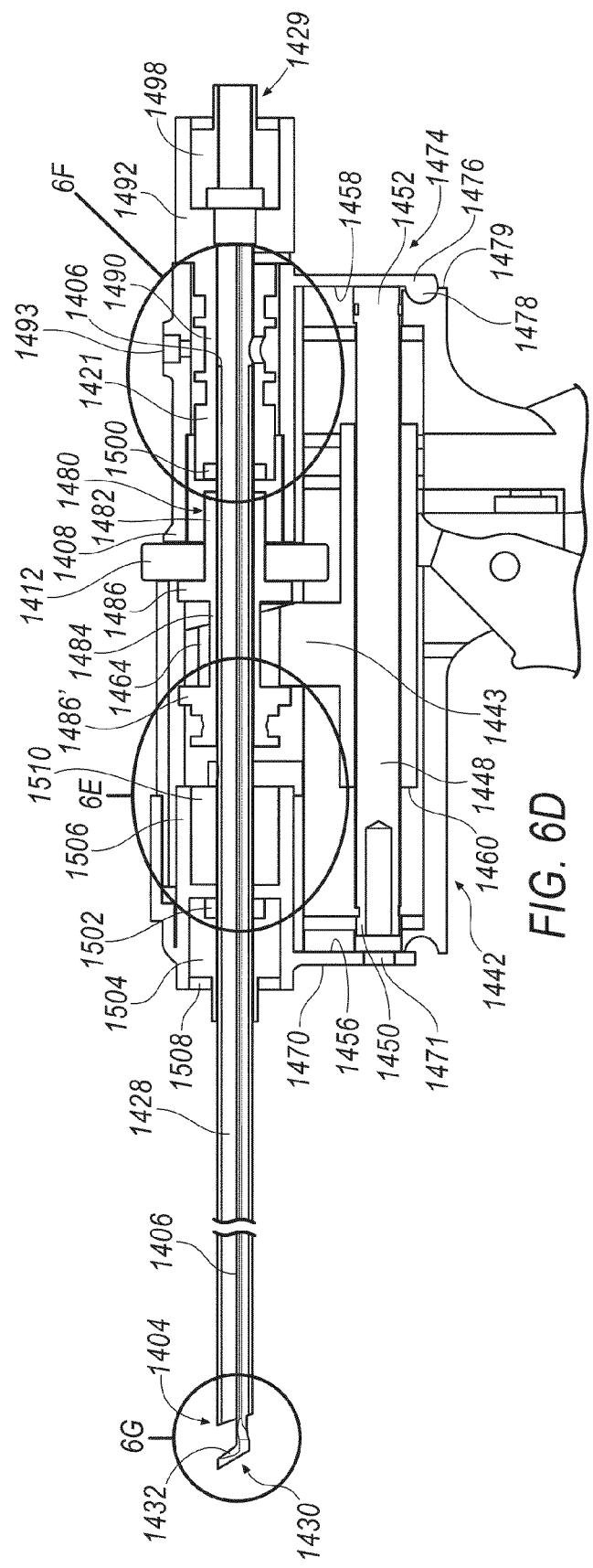
FIG. 6D is a cross-sectional view of the irrigating suction device of FIG. 6A.

Referring to FIG. 6D, disposed within outer cannula 1402 is an inner blade 1416. Inner blade 1416 is axially fixed with respect to housing 1408, such that it does not reciprocate. In one exemplary embodiment, (shown in FIGS. 6D and 6F), a proximal end 1418 of inner blade 1416 includes an attachment lip 1419 that is fixed to a portion of a saline hub 1421 (to be described in further detail below) positioned in housing 1408. In another exemplary embodiment, proximal end 1418 may be formed with an attachment hole (not shown) that aligns with attachment passage 1420, wherein both the attachment hole and the attachment passage receive an attachment mechanism, such as a pin.

Figure 6F:
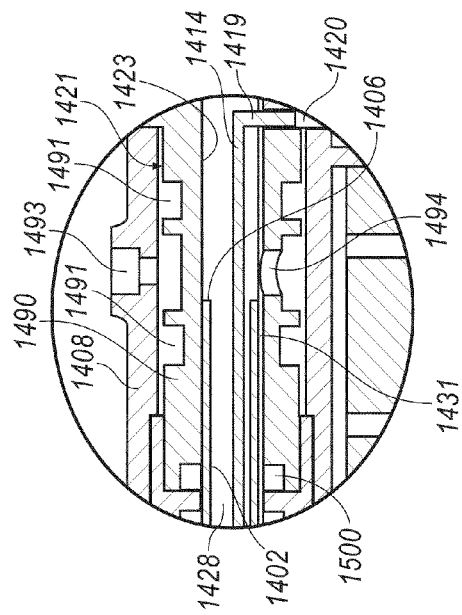
FIG. 6F is an enlarged cross-sectional view of area 6F from FIG. 6D.
Figure 6H:
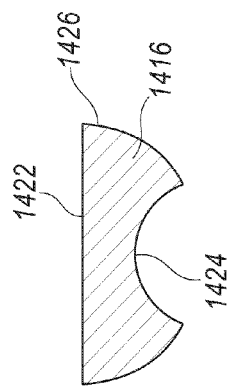
FIG. 6H is a cross-sectional view of an inner blade taken along lines 6H-6H in FIG. 6G.
Figure 6E:
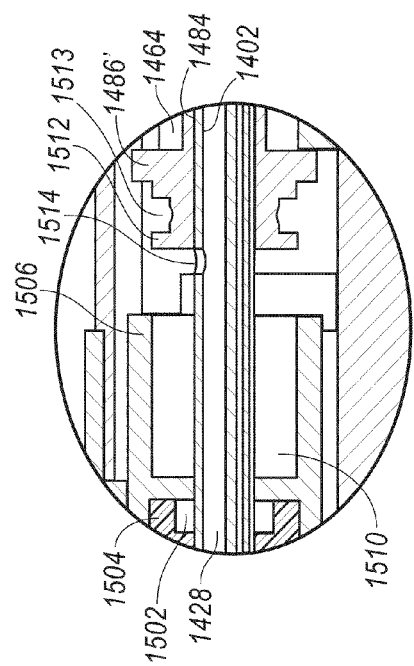
FIG. 6E is an enlarged cross-sectional view of area 6E from FIG. 6D.
Figure 6G:
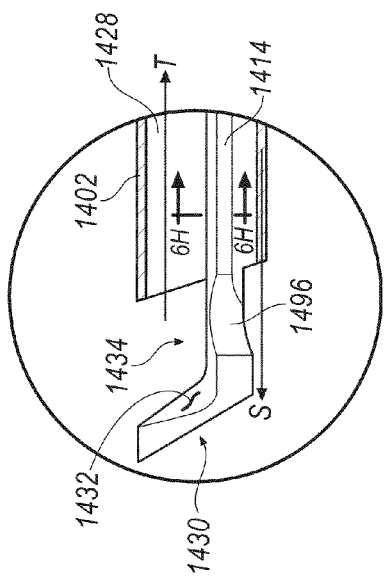
FIG. 6G is an enlarged cross-sectional view of area 6G from FIG. 6D.

FIG. 6H illustrates a cross-section of inner blade 1416 taken along lines H-H in FIG. 6G. Inner blade 1416 is defined by a top surface 1422, a grooved surface 1424, and a curved bearing surface 1426. Top surface 1422 cooperates with an inner lumen 1428 of outer cannula 1402 to form a tissue passage (to be explained in further detail below). Grooved surface 1424 cooperates with inner lumen 1428 of outer cannula 1402 to form a saline passage. Positioned adjacent a distal end 1430 is a saline opening 1496 that is in communication with the saline passage. Curved bearing surface 1426 generally corresponds to the contour of inner lumen 1428. A portion 1431 of curved bearing surface 1426 serves as a glue surface to fixedly attach inner blade 1416 to saline hub 1421. Indeed, inner blade 1416 is fixedly secured to an inner surface of saline hub 1421, which is mounted in housing 1408, such that inner blade 1416 is axially fixed with respect to housing 1408. end 1430 is a saline opening 1496 that is in communication with the saline passage. Curved bearing surface 1426 generally corresponds to the contour of inner lumen 1428. A portion 1431 of curved bearing surface 1426 serves as a glue surface to fixedly attach inner blade 1416 to saline hub 1421. Indeed, inner blade 1416 is fixedly secured to an inner surface of saline hub 1421, which is mounted in housing 1408, such that inner blade 1416 is axially fixed with respect to housing 1408.

A distal end 1430 of inner blade 1416 includes a cutting surface 1432 that extends upwardly from top surface 1422. Cutting surface 1432 cooperates with cutting edge 1414 of outer cannula 1402 to sever tissue that is received within a gap 1434 formed between distal end 1430 of inner blade 1416 and distal end 1404 of outer cannula 1402.

Referring to FIG. 6A, housing member 1408 is mounted to an actuation member 1436. Actuation member 1436 comprises a first handle device 1438 and a second handle device 1440. First handle device 1438 is fixedly connected to a shuttle housing 1442. In one exemplary configuration, shuttle housing 1442 is integrally formed with first handle device 1438. First handle device 1438 may be configured with a thumb grip (not shown), similar to that shown in FIG. 5A (438).

Second handle device 1440 is pivotally connected to a shuttle member 1443 disposed within shuttle housing 1442. Second handle device 1440 may be configured with gripping members 1444, 1446.

Referring to FIG. 6D, shuttle member 1443 is mounted on a rod 1448 disposed in shuttle housing 1442. Rod 1448 is defined by a distal end 1450 and a proximal end 1452. Distal end 1450 is fixedly secured to an interior distal face 1456 of shuttle housing 1442. Proximal end 1452 is fixedly secured to an interior proximal face 1458 of shuttle housing 1442. A biasing member (not shown) is positioned on rod 1448 distally of shuttle member 1443, so as to abut distal face 1456 and a distal end 1460 of shuttle member 1443. Biasing member (which may be a coil spring) serves to bias shuttle member 1443 into a retracted position, away from distal face 1456. A stop member (not shown) may be secured to proximal end 1452 of rod 1448 to limit the distance that shuttle member 1443 may be retracted by the biasing member.

Carried by, and fixedly secured to shuttle member 1443 is a carrier member 1464. Carrier member 1464 is similar to carrier member 464 shown in FIG. 5D, and includes upwardly extending wall members that flank a mounting groove. Carrier member 1464 extends upwardly from shuttle housing 1442.

Housing member 1408 is secured to shuttle member 1443. As best seen in FIG. 6D, in one exemplary arrangement, housing member 1408 includes a mounting flange 1470 that extends downwardly from housing member 1408. A fastening device (not shown) is engaged through a mounting channel 1471 that extends through mounting flange 1470. The fastening device further extends through rod 1448 to secure rod 1448 to housing member 1408.

A proximal end 1474 of housing member 1408 further includes a downwardly extending wall member 1476 that may carry a locking tab 1478. Locking tab 1478 engages with a mounting groove 1479 formed on a proximal face of shuttle member 1443.

Disposed within housing member 1408 is mounting sleeve 1480. Mounting sleeve 1480 comprises an elongated section 1482 that is connected to a mounting section 1484. Disposed on either side of mounting section 1484 are flange members 1486 and 1486'. Mounting section 1484 is received within a mounting groove formed on carrier member 1464. Extending through mounting flanges 1486, 1486' and mounting sleeve 1480 is a passage that receives outer cannula 1402. Outer cannula 1402 is fixedly secured within the passage. In one exemplary arrangement, outer cannula 1402 may be fixedly secured within the passage by glue. Fixedly secured to an outer surface of elongated section 1482 of mounting sleeve 1480 is rotation dial 1412. With this arrangement, as rotation dial 1412 is rotated, mounting sleeve 1480 will rotate, as well. Further, because outer cannula 1402 is fixed secured to mounting sleeve 1480, as rotation dial 1412 is rotated, outer cannula 1402 will also rotate.

Referring now to FIG. 6F, saline hub 1421 will now be described. Saline hub 1421 includes an internal hub portion 1490 and an external hub portion 1492 (best seen in FIG. 6D). Saline hub 1421 is mounted to proximal end 1474 of housing 1402 such that internal hub portion 1490 is disposed within housing 1408. A channel 1423 extends through saline hub 1421 and is in communication with an irrigation opening 1494 formed through saline hub 1421. Channel 1423 is configured to receive outer cannula 1402. Outer cannula 1402 is mounted within channel 1423 for sliding engagement. Inner blade 1414 is also received within channel 1423, as described above. Inner lumen 1428 of outer cannula 1402 opens into channel 1423 at distal end 1406 of outer cannula 1402.

Formed through housing member 1408 is an irrigation port 1493. Irrigation port 1493 is operatively connected to an irrigation line 1495 and is in communication with irrigation opening 1494 in saline hub 1421. In operation, irrigation (such as warm water or saline) enters into housing member 1408 and into saline hub 1421 to deliver irrigation within the space between inner blade 1414 and outer cannula 1402, along a channel formed by grooved surface 1424 and inner lumen 1428. Irrigation flows up through a saline opening 1496 formed in distal end 1430 of inner blade 1414 to deliver irrigation within gap 1434 between inner blade 1414 and outer cannula 1402. Sealing members (not shown), such as O-rings, may be disposed in grooves 1491 disposed on either side of irrigation opening 1494 to insure that the irrigation is directed to the channel formed by grooved surface 1424 and inner lumen 1428 of outer cannula 1402.

Disposed at proximal end 1474 of suction punch 1400 is a fitting member 1498 that is disposed in external hub portion 1492. Fitting member 1498 carries a fitting barb 1499. A vacuum line (not shown) is connected to the fitting barb 1499 to deliver vacuum to outer cannula 1402. To insure that vacuum is delivered to outer cannula 1402, and ultimately to a distal end 1404 of outer cannula 1402, suction punch 1400 is provided with seal members disposed within housing 1408. More specifically, in one exemplary arrangement, saline hub 1421 is provided with grooves 1500 disposed at a distal end thereof that receives seal members (not shown). And additional set of grooves 1502 is provided in a distal housing hub 1504 (shown in FIG. 6D). Distal housing hub 1504 is mounted in a first mounting portion 1506 of housing 1408. First mounting portion 1506 further includes a distal chamber 1508 and a proximal chamber 1510. Distal housing hub 1504 is mounted in distal chamber 1508. Proximal chamber 1510 is configured to receive a distal sealing end 1512 of mounting sleeve 1480. A mounting groove 1513 is formed between distal sealing end 1512 and flange member 1486'. Mounting groove 1513 receives a sealing member (not shown) such as an O-ring. In one embodiment, positioned adjacent to mounting sleeve 1480 is a venting aperture 1514 (best seen in FIG. 6E). Venting aperture 1514 extends through a sidewall of outer cannula 1402.

During operation of suction device 1400, second handle device 1440 is retracted towards first handle device 1438. This action causes shuttle member 1443 to move forward, against the biasing member. As shuttle member 1443 moves forward, carrier member 1464 pushes against one of the flanges 1486' of mounting sleeve 1480. Because mounting sleeve 1480 is fixedly secured to an outer surface of outer cannula 1402, outer cannula 1402 is advanced distally over inner blade 1414, until distal end 1404 of outer cannula 1402 contacts cutting surface 1432 of inner blade 1414, thereby severing tissue that is disposed with gap 1434 defined between inner blade 1414 and distal end 1414 of outer cannula 1402 (see FIG. 6B). Repeated retraction and releasing of second handle device 1440 results in repeated cutting action.

To facilitate collection of tissue, vacuum is delivered to outer cannula 1402 through a vacuum line attached to fitting barb 1499. The vacuum serves to draw tissue into outer cannula 1402, as well as remove cut tissue to a collection chamber (not shown) attached to the vacuum line. Continuous vacuum permits multiple severing actions to be employed with a single insertion. However, delivery of continuous vacuum may be controlled by the action of the cutting cannula. More specifically, the action of the inner cutting cannula provides for a venting operation that relieves vacuum. As such, the device is particularly useful in navigating near and around critical structures within the patient so as not to inadvertently remove such structures during procedures. In addition, by providing the capability of multiple severing actions, procedure time may be reduced.

To alleviate removed tissue occluding the aspiration pathway during the cutting action, irrigation may be provided via an irrigation port 1493 that is connected to an irrigation supply by irrigation line 1495, between inner blade 1414 and outer cannula 1402. The irrigation fluid, which may be warm water or saline, can flow up through opening 1496 in inner blade 1414. Such fluid serves to flush the tissue during the procedure. To provide flexibility, such as to access turbinates 12 in an endonasal procedure, rotation dial 1412 permits the user to selectively rotate inner blade 1414 and outer cannula 1402 to a desired location within a body cavity.

Suction punch 1400 may also provide vacuum relief during operation. During the cutting stroke, as second handle device 1440 is actuated and distal end 1404 of outer cannula 1402 is moved toward cutting surface 1432 of inner blade 1414, distal sealing end 1512 of mounting sleeve 1480 moves into proximal chamber 1510 of first mounting portion 1506 until flange member 1486' abuts first mounting portion 1506, with a sealing member (disposed within mounting groove 1513) contacting an inner surface of proximal chamber 1510. Venting aperture 1514, which is positioned distally of distal sealing end 1512, is thus sealed off while outer cannula 1402 is engaged with cutting surface 1432 of inner blade, providing full vacuum to deliver severed tissue through outer cannula 1402.

To provide vacuum relief, as second handle device 1440 is returned to its non-actuated position (i.e., away from first handle device 1438) by the biasing member, distal sealing end 1512 of mounting sleeve 1480 is moved out of proximal chamber 1510, thereby allowing vacuum delivered through outer cannula 1402 to vent through vent aperture 1514.

Figure 6K:
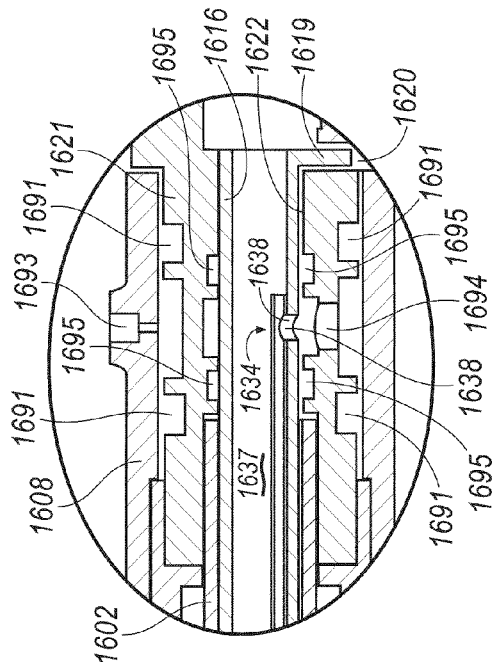
FIG. 6K is a partial cross-sectional view of an alternative arrangement of a saline hub.
Figure 6J:
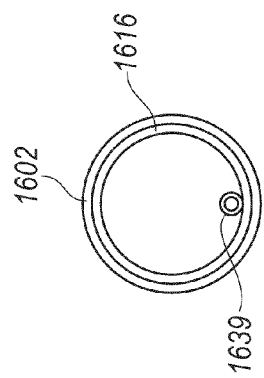
FIG. 6J is a cross-sectional view of the distal end taken along lines 6J-6J of FIG. 6I.
Figure 6I:
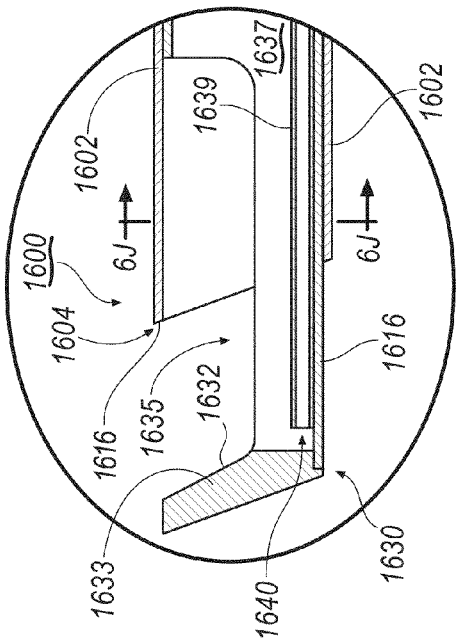
FIG. 6I is a partial cross-sectional view of a distal end of an alternative arrangement of an irrigation suction punch.

Turning to FIGS. 6I-6K, partial illustrations of an alternative configuration of a suction punch 1600 are shown. Suction punch 1600 is very similar to suction punch 1400 and includes an outer cannula 1602 that is configured similar to outer cannula 1402. Outer cannula 1602 is defined by a distal end 1604 and a proximal end 1606 (see in FIG. 6K), which is seated within a housing member similar to housing member 1408. Distal end 1604 is open and may have an angled cutting edge 1614 to provide increased cutting effectiveness. Outer cannula 1602 is configured for both selective rotational movement and reciprocal movement by an actuation assembly, as described above in connection with suction punch 1400.

Disposed within outer cannula 1602 is an inner cannula 1616. In the configuration shown in FIG. 6I, inner cannula 1616 replaces inner blade 1416. Inner cannula 1616 is axially fixed with respect to the housing, such that it does not reciprocate. In one exemplary arrangement, a portion of a proximal end 1619 of inner cannula 1616 includes an outwardly extending mounting member that may be received within a portion of a saline hub 1621 positioned in housing 1608 (see, e.g., FIG. 6K). In one configuration, the mounting member is received within a mounting groove 1620. The mounting member may be secured within mounting groove 1620 with glue to fixedly attach inner cannula 1616 to housing 1408. A portion of an outer surface of inner cannula 1616 may serve as a glue surface to fixedly attach inner cannula 1616 to a portion of an inner surface 1622 of saline hub 1621, which is mounted in housing 1408, such that inner cannula 1616 is axially fixed with respect to housing 1408.

Inner cannula 1616 further is defined by a distal end 1630, which includes a cutting surface 1632 disposed on a tip 1633 thereof. A tissue receiving opening 1635 is formed adjacent tip 1633. Cutting surface 1632 cooperates with cutting edge 1614 of outer cannula 1602 to sever tissue that is received within tissue receiving opening 1635. Tissue receiving opening 1635 opens into a tissue passage 1637. Tissue passage 1637 is operatively connected to a vacuum supply. Vacuum supply operates to deliver severed tissue through the housing and to a collection canister.

Fixedly disposed within inner cannula 1616 is an irrigation supply tube 1639. In one exemplary configuration, irrigation supply tube 1639 is positioned along a bottom portion of inner cannula 1616 and has a distal end 1640 that is positioned adjacent cutting surface 1632. A proximal end 1634 of irrigation supply tube 1639 is in fluid communication with an irrigation opening 1694 disposed within saline hub 1621. More specifically, irrigation supply tube 1639 includes an opening 1636 formed in a sidewall that aligns with a corresponding opening 1638 formed inner cannula 1616. While irrigation supply tube 1639 is shown as being positioned along a bottom portion of inner cannula 1616, it is understand that the disclosure is not limited to that configuration. For example, and without limitation, irrigation supply tube 1639 may also be positioned along a top portion of inner cannula 1616 such that distal end 1640 is positioned at tissue opening 1635.

Referring now to FIG. 6K, saline hub 1621 will now be described. Saline hub 1621 includes an internal hub portion 1690. Saline hub 1621 is mounted to a proximal end of housing 1402 such that internal hub portion 1690 is disposed within housing 1408. A channel, defined by inner surface 1622 of saline hub 1621 extends through saline hub 1621. The channel is configured to receive outer cannula 1602. Outer cannula 1602 is mounted within the channel for sliding engagement. Inner cannula 1614 is also received within the channel, as described above.

Formed through housing member 1608 is an irrigation port 1693. Irrigation port 1693 is operatively connected to an irrigation line and is in communication with irrigation opening 1694 in saline hub 1621. In operation, irrigation (such as warm water or saline) enters into housing member 1608 and into saline hub 1621 to deliver irrigation to irrigation supply tube 1639. To direct irrigation fluid into irrigation supply tube 1639, sealing members (not shown), such as O-rings, may be disposed in grooves 1691, 1695 disposed on either side of irrigation opening 1694. More specifically, grooves 1691 are disposed in an outer surface of saline hub 1621 such that a sealing member disposed therein serves to prevent irrigation fluid from entering between saline hub 1621 and housing 1608. Grooves 1695 are disposed in inner surface 1622 of saline hub 1621 such that a sealing member disposed therein serves to prevent irrigation fluid from entering between inner and outer cannulas 1616, 1602.

B. Saw Device

As discussed above, once a pathway is cleared, (such as a pathway through the nasal cavity 14), a section of the sella turscica 26 must be removed to create an opening to the brain. A burring device (such as that shown in FIG. 11A) is activated to create a small opening 800 in the sella turscica 26. Once the opening 800 is formed a saw device (or burring device 700, as will be explained later) is inserted into opening 800 and activated to cut out a section 804 of the sella turscica 26.

A first embodiment of a saw device 520 is shown in FIGS. 8A-8. Saw device 520 comprises a driveshaft 522 that is slidably attached to a spindle 524. Operatively attached to a distal end 526 of driveshaft 522 is a first gear mechanism 528 that cooperates with a second gear mechanism 530 that is operatively connected to a blade member 532 that includes a blade 534. Spindle 524 is pivotally attached to blade member 532.

Disposed within driveshaft 522 is an irrigation shaft 536 having a closed first end 537. An open second end 538 of irrigation shaft 536 is operatively attached to an irrigation supply (not shown) by suitable tubing. Irrigation shaft 536 extends through driveshaft and into a sleeve member 540 that is fixedly connected to driveshaft 522. Sleeve member 540 carries first gear mechanism 528. A small opening 542 is formed in sleeve member 540 and oriented so as to face blade 534. Opening 542 is in communication with an interior of irrigation shaft 536. Thus, as irrigation is directed through irrigation shaft 536, it is delivered to blade 534.

Irrigation shaft 536 is sized to be smaller than an interior surface 544 of driveshaft 524, thereby creating a gap 546 between interior surface 544 and an outer surface 548 of irrigation shaft 536. Gap 546 terminates at a proximal end 548 of driveshaft 522 and may be operatively connected to a vacuum supply (not shown) by suitable tubing.

In operation, driveshaft 522 is connected to a power supply (not shown) that rotates driveshaft 522 as indicated by arrow R shown in FIG. 9. As driveshaft 52 rotates, first gear mechanism 528 engages with second gear mechanism 530 to rotate blade member 532, and hence blade 534. In one exemplary embodiment, blade member 532 is a diamond dusted to provide for a robust cutting surface.

As blade member 532 is rotated, irrigation is supplied through irrigation shaft 536, as indicated by arrows I in FIG. 8A. Irrigation is delivered to opening 542 to minimize dust particles within the surgical field.

Vacuum is also supplied to gap 546, which is open where driveshaft 522 contacts spindle 524. The vacuum picks up any stray debris generated by the cutting action of blade 534 against the sella turcica 26 to draw such debris out of the surgical field, as indicated by arrows V in FIG. 8A.

Another embodiment of a saw device 600 is shown in FIGS. 10A-10C. Saw device 600 comprises a housing portion 602, a belt member 604, and a depth stop 606. Housing portion 602 is pivotally connected to depth stop 606 at pivot point P to permit selective positioning of saw device 600 during operation.

Disposed at a distal end 608 of housing portion 602 is a pulley member 610. Pulley member 610 is configured to be engaged with sections of belt member 604 to assist with operation of belt member 604. Pulley member 610 is operatively connected to a motor source (not show) to rotate pulley member 610. A corresponding follower pulley member (not shown) is positioned on a proximal end of saw device 600, within housing portion 602. Belt member 604 is wound around pulley member 610 and follower pulley member such that a portion of belt member 604 is disposed within housing portion 602. Rotation of pulley member 610 causes belt member 604 move.

Belt member 604 is configured with a cutting surface 612. Cutting surface 612 may be diamond dusted to provide sufficient strength to cut through bone.

In addition to belt member 604, housing portion 604 may further comprise either an irrigation port or a vacuum port, or a combination of both. In one exemplary embodiment (shown in FIGS. 10A and 10B), housing portion 602 is configured with at least one hollow vacuum port 614 that is in communication with a vacuum supply (not shown) at a proximal end and in communication with belt member 604 adjacent a distal end 616 of housing portion 602. In one embodiment, vacuum port 614 is positioned outwardly of belt member 604. In another embodiment, housing portion 604 comprises a pair of vacuum ports 614 disposed on either side of housing portion 604. However, it is also understood that vacuum port 614 may be positioned in an interior chamber 618 of housing portion 600. Vacuum port 614 operates to remove debris generated by the cutting action of saw device 600.

Saw device 600 may also include an irrigation port 620. In one exemplary embodiment, irrigation port 620 is positioned in interior chamber 618. A proximal end of irrigation port 620 is operatively connected to an irrigation supply (not shown). A distal end 622 of irrigation port 620 is positioned adjacent pulley 610 such that irrigation may be supplied to cutting surface 612 as saw device operates.

In yet another alternative embodiment (not shown), irrigation port 620 may be positioned outwardly of belt member 604. For example, an irrigation port 620 may be positioned on either side of housing 602, with a vacuum port 614 positioned in the central region of housing 602. In yet another alternative embodiment (not shown), on one side of housing 602 a vacuum port 614 may be positioned, with an irrigation port 620 on an opposite side of housing 602.

Referring now to FIGS. 11A-11B, yet another embodiment of a saw device 700 is shown. Saw device 700 comprises a housing 702 that supports a tip member 704. Tip member 704 is rotatably supported by housing 702 such that it rotates 360°. A power source (not shown) is operatively connected to tip member 704 to rotate tip member 704 during use. Tip member 704 includes a non-abrasive distal end 706 and an abrasive cutting surface 708. In one embodiment, abrasive cutting surface 708 is diamond dusted to provide sufficient strength to cut through bone. Non-abrasive distal end 706 serves may be configured as a polished ball end to prevent inadvertent damage to the dura as abrasive cutting surface 708 cuts through bone.

Housing 702 may be provided with a depth stop 707 positioned at a distal end of housing 702. Depth stop 707 serves to limit the depth that tip member 704 may be extended into a patient. Housing 702 may further comprise either an irrigation port or a vacuum port, or a combination of both. In one exemplary embodiment (shown in FIGS. 11A and 11B), housing portion 702 is configured with at least one hollow vacuum port 714 that is in communication with a vacuum supply (not shown) at a proximal end and in communication with tip member 704 adjacent a distal end 716 of housing 702. In one embodiment, housing 702 comprises a pair of vacuum ports 714 disposed on either side of housing 702. However, it is also understood that vacuum port 714 may be positioned in an interior chamber 718 of housing 702. Vacuum port 714 operates to remove debris generated by the cutting action of saw device 700.

As discussed above, saw device 700 may also include at least one irrigation port 720. In one exemplary embodiment, irrigation port 720 is positioned in interior chamber 718. A proximal end of irrigation port 720 is operatively connected to an irrigation supply (not shown). A distal end 722 of irrigation port 720 is positioned adjacent tip member 704 such that irrigation may be supplied to cutting surface 708 as saw device operates.

In yet another alternative embodiment (not shown), irrigation port 720 may be positioned on either side of housing 702, with a vacuum port 714 positioned in interior chamber 718 of housing 702. In yet another alternative embodiment (not shown), on one side of housing 702 a vacuum port 714 may be positioned, with an irrigation port 720 on an opposite side of housing 702.

In yet a further embodiment of saw device 800, as shown in FIG. 12, tip member 802 may be configured so as to include one or more irrigation channels 805 extending therethrough. An irrigation port 820 is fluidly connected to an interior of tip member 802 such that irrigation fluid flows though irrigation channels 805 during operation of saw device 800.

C. Scissors

Turning now to FIG. 7, a representative embodiment of scissors 900 is shown. Scissors 900 comprise a first leg member 902 and a second leg member 904. First leg member 902 includes a blunt edge 906, while second leg member 904 includes a cutting edge 908. The blunt edge 906 and the cutting edge 908 are disposed at a distal end of first and second leg members 902, 904, respectively.

A proximal end 910 of first leg member 902 is fixedly connected to a handle 912. In one embodiment, proximal end 910 is connected to handle 912 via a removable fastener 914 such that first leg member 902 may be detached from handle 912. Similarly, second leg member 904 may also be removably connected to handle 912.

However, second leg member 904 is also connected to handle 912 for reciprocating motion, as indicated by arrow A. Such action brings cutting edge 908 into contact with blunt edge 906 to cut brain tissue. The reciprocating motion is effectuated by a cam member 916 that is operated by a motor 918. The cam member 916 cooperates with a follower member 920 formed on a proximal end 922 of second leg member 904. A spring member 924 serves to bias cutting edge 908 away from blunt edge 906. A tongue 926 and groove 928 arrangement serves to maintain the relative positions of first and second leg members 902 and 904 during the reciprocating motion.

D. Tissue Resection Device

Referring to FIG. 13, an exemplary tissue cutting device 40 includes a handpiece 42 and an outer cannula 44 that cooperates with an inner cutting cannula disposed therein to sever tissue. Handpiece 42 includes a lower housing 50 which comprises a proximal section 46 and distal section 48. An upper housing 52 is also provided. A tissue collector 58 may be operatively connected to upper housing 52. A rotation dial 60 for rotating the outer cannula 44 with respect to handpiece 50 is also mounted to upper housing 52. Additional details concerning the configuration and operation of the tissue cutting device 40 is set forth in co-pending and commonly owned U.S. application Ser. No. 12/336,054, the contents of which are incorporated by reference in its entirety.

E. Dispensing Wand

Referring now to FIG. 14, an exemplary embodiment of a dispensing wand 950 is shown. Dispensing wand 950 comprises a dispensing tip 952 a handle portion 954 and a sealant conduit 956. Conduit 956 is operatively connected to a sealant supply. In operation, sealant is delivered through conduit 956 and out of dispensing tip 952. In one embodiment, dispensing tip 952 includes a flexible portion 958 to allow greater accuracy in delivering sealant to the desired location.

It will be appreciated that the system and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed is:

1. A method for conducting a surgical procedure, comprising:
    creating a pathway through a nasal cavity;
    creating an opening through a section of skull that is connected to the nasal cavity;
    harvesting a section of the skull formed by creating the opening to expose a dura layer of the brain, wherein the harvested section is maintained in a unitary structure, defined by a periphery;
    cutting a section of the dura layer to expose a section of brain tissue;
    inserting a tissue resection device through the nasal cavity to take tissue samples from the exposed brain tissue;
    securing the dura layer over the exposed brain tissue so as to create a watertight seal; and
    inserting the harvested section of the skull in the opening and securing the harvested section to the skull to close the opening.

2. The method of claim 1, wherein the pathway through the nasal cavity is created by removing at least one turbinate.

3. The method of claim 2, wherein the pathway is created by using a suction punch to remove the turbinates.

4. The method of claim 3, wherein the suction punch delivers vacuum to the turbinate during the creation of the pathway to draw at least a section of the turbinate into the suction punch.

5. The method of claim 4, wherein the suction punch removes multiple sections of the turbinate with a single insertion of the suction punch.

6. The method of claim 3, wherein the suction punch delivers an irrigation fluid to the turbinate during creation of the pathway.

7. The method of claim 6, wherein the irrigation fluid is one of saline, warm saline, water, and lactating ringers.

8. The method of claim 1, wherein the creation of the opening further comprises forming a starter hole that is sized to be substantially smaller than the opening.

9. The method of claim 8, wherein a saw device is inserted into the starter hole and operated to cut the opening.

10. The method of claim 9, wherein the saw device delivers an irrigation fluid to a cutting surface of the saw device.

11. The method of claim 9, wherein the saw device delivers vacuum to a cutting surface of the saw device to remove debris created by the cutting of the opening.

12. The method of claim 1, wherein surgical scissors are used to cut the dura layer.

13. The method of claim 1, wherein the dura layer is cut so as to form a flap having at least a portion that remains attached to an uncut dura layer section.

14. The method of claim 13, wherein the flap is retracted away from the uncut dura layer section.

15. The method of claim 1, wherein the step of securing the dura layer over the exposed brain tissue further comprises applying a securing agent along a peripheral edge of a cut-out section of the dura layer to secure the cut-out section of the dura layer to a remaining section of the dura layer.

16. The method of claim 15, wherein the securing agent is a biocompatible glue.

17. The method of claim 15, further comprising placing a collagen matrix graft over the cut section of the dura layer, whereby the securing agent secures the graft to the dura layer.

18. The method of claim 1, wherein the harvested section of the skull is secured within the opening by a securing agent.

19. The method of claim 18, wherein the securing agent includes a bio-compatible glue.

* * * * *